United States Patent [19]

Salmon et al.

[11] Patent Number: 5,187,176

[45] Date of Patent: Feb. 16, 1993

[54] 1-PHENYL SUBSTITUTED PYRIMIDONE DERIVATIVES

[75] Inventors: Roger Salmon, Bracknell; Raymond L. Sunley; Alan J. Whittle, both of Twyford, all of England

[73] Assignee: Imperial Chemical Industries PLC, London, England

[21] Appl. No.: 775,677

[22] Filed: Oct. 9, 1991

[30] Foreign Application Priority Data

Oct. 16, 1990 [GB] United Kingdom ............... 9022444

[51] Int. Cl.$^5$ .................... A01N 43/54; C07D 239/06
[52] U.S. Cl. .................... 514/269; 514/272; 514/274; 514/344; 514/349; 514/350; 514/351; 544/301; 544/311; 544/312; 544/319; 544/321; 546/287; 546/288; 546/289; 546/293; 546/294; 546/295; 546/296; 546/297; 546/298; 546/300; 546/301; 546/302; 548/263.2; 548/263.8; 548/264.8; 548/267.8; 548/269.4; 548/375; 548/378
[58] Field of Search ............... 544/301, 311, 312, 319, 544/321; 514/269, 272, 274

[56] References Cited

U.S. PATENT DOCUMENTS 4,147,528   4/1970  McNulty et al. .................... 71/92

FOREIGN PATENT DOCUMENTS 0259048   3/1988  European Pat. Off. .
0285893  10/1988  European Pat. Off. .
0338686  10/1989  European Pat. Off. .
0398499  11/1990  European Pat. Off. .
8903825   5/1989  World Int. Prop. O. .......... 544/311

Primary Examiner—Mukund J. Shaw
Assistant Examiner—Jyothsna Venkat
Attorney, Agent, or Firm—William E. Dickheiser

[57] ABSTRACT

Phenyl substituted heterocyclic compounds having insecticidal activity have the formula (I):

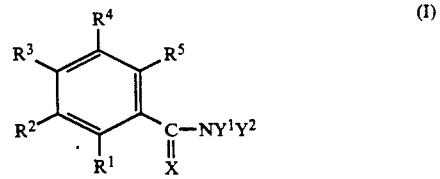

wherein $R^1$ is an optionally substituted pyridone, thiopyridone, pyrimidinthione, pyrimidinone, pyrazole, imidazole or triazole group; $R^2$ is hydrogen, halogen, haloalkyl, nitro, cyano or a group $-CX-NY^1Y^2$; $R^3$ and $R^5$ are hydrogen, halogen, alkyl or cycloalkyl; $R^4$ is halogen, haloalkyl, haloalkoxy or $S(O)_nR^6$; and $Y^1$ and $Y^2$ are independently selected from hydrogen, nitro, amino or optionally substituted alkyl or $Y^1$ and $Y^2$ together with the nitrogen to which they are attached form an aliphatic heterocyclic group or form the group $=CHY^3$ or $Y^1$ is hydrogen and $Y^2$ is alkoxycarbonyl, alkylcarbonyl, optionally substituted aralkyl or $-S(O)_nR^6$.

9 Claims, No Drawings

1-PHENYL SUBSTITUTED PYRIMIDONE DERIVATIVES

The present invention relates to novel phenyl substituted heterocyclic compounds which have insecticidal activity, to processes for their preparation and to their use as insecticides.

According to the present invention there is provided an insecticidal compound of formula (I), wherein $R^1$ is optionally substituted pyridone, thiopyridone, pyrimidinthione, pyrimidinone, pyrazole, imidazole or triazole group; $R^2$ is hydrogen, halogen, haloalkyl, nitro, cyano or a group —CX—$NY^1Y^2$ as hereinafter defined; $R^3$ and $R^5$ are independently selected from hydrogen, halogen, alkyl or cycloalkyl; $R^4$ is halogen, haloalkyl, haloalkoxy or $S(O)_nR^6$ where $R^6$ is alkyl, haloalkyl or cycloalkyl and n is 0, 1 or 2; X is O or S or S=O; and $Y^1$ and $Y^2$ are independently selected from hydrogen, nitro, amino or alkyl optionally substituted by halogen, by cycloalkyl, by formyl, by $C_{2-7}$ alkanoyl, by $C_{4-7}$ cycloalkylcarbonyl, by $C_{2-7}$ alkoxycarbonyl, by $C_{2-7}$ haloalkoxycarbonyl, by an aryl group or by an aromatic heterocyclic group or $Y^1$ and $Y^2$ together with the nitrogen to which they are attached form an aliphatic heterocyclic group containing from 4 to 8 atoms in the ring and optionally substituted by halogen or alkyl or $Y^1$ and $Y^2$ together form the group =$CHY^3$ wherein $Y^3$ is alkyl, $C_{2-6}$ alkenyl, aryl, an aromatic heterocycle, or amino optionally substituted by alkyl or $Y^1$ is hydrogen and $Y^2$ is alkoxycarbonyl, alkylcarbonyl, optionally substituted aralkyl or a group —$S(O)_nR^6$ where $R^6$ and n are as hereinbefore defined.

The term "alkyl" is used herein includes straight or branched chain alkyl groups, preferably containing up to 6 carbon atoms. This applies also to alkyl moieties contained in "haloalkyl" groups. The term "cycloalkyl" used herein refers to a carbocyclic ring suitably having from 3 to 10 and preferably from 3 to 7 carbon atoms in the ring. The cycloalkyl group is preferably cyclopropyl.

Suitable halogen groups, $R^2$, $R^3$, $R^4$ and $R^5$ include fluorine, chlorine, bromine or iodine.

Suitable haloalkyl groups for $R^2$, $R^4$ and $R^6$ are $C_1$–$C_4$ alkyl groups substituted with chlorine, fluorine, bromine or iodine. Such groups may include di- and trihalomethyl groups in particular trifluoromethyl, and pentahaloethyl groups, in particular pentafluoroethyl. Such groups may also include two or more different halogens.

Suitable haloalkoxy groups for $R^4$ include $C_1$–$C_4$ haloalkoxy groups, substituted with fluorine, chlorine, bromine, or iodine. Such groups may also include two or more different halogens. As examples of such haloalkyoxy groups there may be mentioned halomethoxy and haloethoxy groups, especially fluormethoxy and fluoroethoxy groups, for example $OCF_3$, $OCF_2H$ and $OCF_2CF_2H$.

Preferably $R^4$ is trifluoromethyl, pentafluoroethyl trifluoromethylthio, iodine, bromine, chlorine, $OCF_3$, $OCF_2H$, $OCF_2CF_2H$, methylthio or $S(O)_nR^6$, for example $CF_3SO$—. It is especially preferred that $R^4$ is trifluoromethyl, or fluoro $C_1$–$C_4$ alkoxy such as $OCF_3$, $OCF_2H$ or $OCF_2CF_2H$.

Preferably $R^2$ is fluorine, chlorine, bromine or trifluoromethyl. It is especially preferred that $R^2$ is fluorine, chlorine or bromine.

Preferably $R^3$ and $R^5$ are hydrogen.

Preferably X is S and $Y^1$ and $Y^2$ are independently selected from hydrogen and alkyl, for example methyl.

An example of group $R^1$ is a group of sub-formula (a), where $R^{10}$ is oxygen or sulphur; $R^{20}$ is hydrogen, halogen, optionally substituted amino, alkyl optionally substituted by halogen, alkoxy optionally substituted by halogen, and thioalkoxy optionally substituted by halogen; $R^{21}$ is hydrogen, halogen, optionally substituted alkyl, optionally substituted alkoxy, optionally substituted thioalkoxy, cyano, nitro, optionally substituted oximino, optionally substituted alkenyl, optionally substituted aryloxy, optionally substituted amino or $S(O)_nR^6$ wherein n and $R^6$ are as hereinbefore defined; $R^{22}$ is hydrogen, or alkyl optionally substituted by halogen, lower alkenyl optionally substituted by halogen or $CO_2R^{37}$ wherein $R^{37}$ is alkyl optionally substituted by halogen; and $R^{23}$ is a group $R^{20}$ as defined above or a cyano or nitro group.

The term "alkenyl" used herein includes groups having from 2 to 6 carbon atoms, preferably 2 or 3 carbon atoms. The term "aryl" includes phenyl.

Examples of $R^{21}$ include hydrogen, halo, lower alkyl optionally substituted by halo or hydroxy; cyano; nitro; oximino optionally substituted by lower alkyl, aryl, lower alkenyl or aralkyl wherein the aryl portion is optionally substituted with halogen or nitro; lower alkenyl optionally substituted by halogen or cyano; amino; or $S(O)_nR^6$ wherein n and $R^6$ are as hereinbefore defined.

Specific examples of $R^{21}$ include hydrogen, iodine, methyl, hydroxymethyl, chloromethyl, trifluoromethyl, pentafluoroethyl, difluoromethyl, dichloromethyl, thiomethyl, ethoxyimino, t-butyloximino, p-nitrobenzyloxyimino, phenoxyimino, pentafluorobenzyloximino, prop-2-enyloxyimino, 2,2-dichloroethenyl, 2-cyanoethenyl, ethynyl or $S(O)CF_3$.

Preferably $R^{21}$ is hydrogen, cyano, trifluoromethyl or pentafluoroethyl.

Suitable groups $R^{22}$ include halo(lower)alkyl, branched chain lower alkyl, halo(lower)alkenyl, or a lower carboxylic ester group.

Examples of suitable groups $R^{22}$ include trifluoromethyl, pentafluoroethyl, 2,2-di-bromoethenyl, ethoxycarbonyl and tert-butyl.

$R^{23}$ is preferably hydrogen, bromine, cyano or nitro,

A further example of the group $R^1$ is a group of sub-formula (b) where $R^{10}$ is oxygen or sulphur; $R^{24}$ is hydrogen, halogen, $NR^7R^8$, $S(O)_nR^6$, alkyl or cycloalkyl wherein $R^7$ and $R^8$ are independently selected from hydrogen, alkyl or cycloalkyl; $R^{25}$ is halo, nitro, haloalkyl, haloalkoxy or $S(O)_nR^6$; and $R^{26}$ is hydrogen, alkyl, halogen, cyano, hydroxyalkyl, alkoxy, $S(O)_nR^6$, haloalkylthio, $NR^{11}R^{12}$, formyl, nitro or haloalkyl.

Suitable halogen groups for $R^{24}$, $R^{25}$ and $R^{26}$ include fluoro, chloro, bromo or iodine.

Suitable haloalkyl groups $R^{25}$, $R^{26}$ and $R^6$ include di- and trihalomethyl groups, in particular trifluoromethyl and pentahaloethyl groups such as pentafluoroethyl.

Preferably $R^{25}$ is trifluoromethyl or pentafluoroethyl.

Preferably $R^{24}$ is hydrogen.

Preferably $R^{26}$ is hydrogen or alkyl.

A further group of compounds of formula $R^1$ are compounds of sub-group (c), wherein $R^{27}$ is hydrogen, alkyl, haloalkyl, $S(O)_nR^6$, cyano, nitro, halogen, $NR^{11}R^{12}$ wherein $R^{11}$ and $R^{12}$ are independently selected from hydrogen or alkyl optionally substituted by $C_{2-5}$ alkoxycarbonyl, or cycloalkyl; $R^{28}$ is halogen; cyano; nitro; cycloalkyl; $C_{2-6}$ alkenyl; thiocyanato; sulphamoyl or carbamoyl either of which may be substituted with one or two alkyl groups; $C_{2-7}$ alkoxycarbonyl; $C_{2-7}$ alkanoyl; alkyl; haloalkyl; or $S(O)_nR^6$ where n and $R^6$ are as hereinbefore defined; $R^{29}$ is hydrogen; $NR^{11}R^{12}$ wherein $R^{11}$ and $R^{12}$ are independently selected from hydrogen or alkyl optionally substituted by $C_{2-5}$ alkoxycarbonyl, cycloalkyl, formyl, $C_{2-7}$ alkanoyl, $C_{4-7}$ cycloalkylcarbonyl, $C_{2-7}$ alkoxycarbonyl, $C_{2-7}$ haloalkoxycarbonyl or $R^{11}$ and $R^{12}$ together with the nitrogen to which they are attached form a pyrrole optionally substituted by halogen; $C_{1-4}$ alkylsulphenylamino; alkoxymethyleneimino; halogen; alkyl; carboxy or salts thereof; alkylthio; alkylsulphinyl; haloalkylsulphinyl; alkylsulphonyl; haloalkylsulphonyl; trialkylmethylsilyl; cyano or nitro.

Any alkyl chains in the above groups may be straight or branched.

Suitable halogen atoms for $R^{27}$ are fluorine, chlorine, bromine or iodine. Particularly preferred compounds are those in which $R^{27}$ is hydrogen, cyano or dialkylamino, for example dimethylamino and $R^{28}$ is $S(O)_nR^6$, for example —$SCF_3$ or —$SOCF_3$. Examples of such compounds include 1-(2-chloro-6-thioamido-4-trifluoromethylphenyl)-3-dimethylamino-4-(trifluoromethylthio)-pyrazole, 1-(2-chloro-6-thioamido-4-trifluoromethylphenyl)-4-(dichlorofluoromethylthio)-pyrazole, 1-(2-chloro-6-thioamidophenyl)-3-cyano-4-trifluoromethylthio)-pyrazole, 1-(2-chloro-6-thioamidophenyl)-4-(trifluoromethylthio)-pyrazole, 1-(2-chloro-6-thioamidophenyl)-3-cyano-4-(trifluoromethylsulphonyloxy)-pyrazole and 1-(2-chloro-6-thioamidophenyl)-4-(trifluoromethylsulphonyloxy)-pyrazole.

A further group $R^1$ is a group of formula (d) wherein $R^{30}$ is hydrogen or alkyl optionally substituted by alkoxy, alkylthio, alkylsulphinyl, alkylsulphonyl, cyano, carboxy or $C_{2-7}$ alkoxycarbonyl; $R^{31}$ and $R^{32}$ are independently selected from hydrogen; halogen; nitro; carboxy; cyano; $C_{2-7}$ alkoxycarbonyl; $C_{2-7}$ alkanoyl; carbamoyl or sulphamoyl either of which may be optionally substituted by one or two alkyl groups; amino optionally substituted by one or two groups selected from alkyl, $C_{2-7}$ alkoxycarbonyl and $C_{2-7}$ alkanoyl; alkyl; haloalkyl or $S(O)_nR^6$ where n and $R^6$ are as hereinbefore defined.

Preferably $R^{30}$ is hydrogen.

Preferably $R^{31}$ and $R^{32}$ are independently selected from cyano, trifluoromethyl, bromo or nitro.

Yet a further group $R^1$ is a group of sub-formula (e) wherein $R^{33}$ is $C_{2-6}$ alkyl optionally substituted by halogen, alkoxy, alkylsulphonyl, alkoxycarbonyl or carbamoyl; cycloalkyl substituted by methyl; $C_{2-6}$ alkenyl; $C_{1-4}$ alkylsulphinyl or 2-methyl-1,3,-dithiolan-2-yl; and $R^{34}$ is hydrogen; halogen; haloalkyl; alkoxyalkyl; $C_{2-6}$ alkenyloxyalkyl, methyl, alkylsulphinyl, alkylsulphonyl; phenyl; $NR^{13}R^{14}$ wherein $R^{13}$ and $R^{14}$ are independently selected from hydrogen, alkyl, alkoxy, acyl such as acetyl, amino, phenyl, $C_{2-6}$ alkenyl, $C_{2-6}$ alkynyl, dimethylcarbanoyl, alkoxycarbonyl, trichloromethylthio, alkylsulphonyl or haloalkylsulphonyl or $R^{13}$ and $R^{14}$ together with the nitrogen atom to which they are attached form a heterocyclic ring such as pyrrole; or —$N=CR^{15}R^{16}$ where $R^{15}$ is hydrogen or alkylthio and $R^{16}$ is alkylthio or alkoxy.

Preferably $R^{33}$ is tert-butyl or pentafluoroethyl.

Preferably $R^{34}$ is dialkylamino, for example, dimethylamino or diethylamino.

It is preferred that $R^1$ is a group of sub-formula (b).

Examples of compounds of formula (I) wherein $R^1$ is a group of sub-formula (b') are set out in Table I below.

TABLE I

| COMPOUND NO. | $R^2$ | $R^3$ | $R^4$ | $R^5$ | X | $Y^1$ | $Y^2$ | $R^{25}$ | $R^{26}$ | $R^{10}$ |
|---|---|---|---|---|---|---|---|---|---|---|
| 1 | Cl | H | $CF_3$ | H | O | H | H | $C_2F_5$ | H | O |
| 2 | Cl | H | $CF_3$ | H | S | H | H | $C_2F_5$ | H | O |
| 3 | Cl | H | $CF_3$ | H | O | H | H | $CF_3$ | H | O |
| 4 | Cl | H | $CF_3$ | H | S | H | H | $CF_3$ | H | O |
| 5 | Br | H | $CF_3$ | H | S | H | H | $CF_3$ | H | O |
| 6 | Br | H | $CF_3$ | H | S | H | H | $C_2F_5$ | H | O |
| 7 | Cl | H | $CF_3$ | H | S | H | H | $CF_3$ | $CH_3$ | O |
| 8 | Br | H | $CF_3$ | H | S | H | H | $C_2F_5$ | $CH_3$ | O |
| 9 | Cl | H | $CF_3$ | H | S | H | H | $C_2F_5$ | $CH_3$ | O |
| 10 | F | H | $CF_3$ | H | S | H | H | $CF_3$ | H | O |
| 11 | F | H | $CF_3$ | H | S | H | H | $C_2F_5$ | $CH_3$ | O |
| 12 | F | H | $CF_3$ | H | S | H | H | $CF_3$ | $CH_3$ | O |
| 13 | F | H | $OCF_2H$ | H | S | H | H | $C_2F_5$ | H | O |
| 14 | Cl | H | $OCF_3$ | H | S | H | H | $CF_3$ | H | O |
| 15 | Cl | H | $OCF_2CF_2H$ | H | S | H | H | $CF_3$ | H | O |
| 16 | Cl | H | $OCF_2H$ | H | S | H | H | $C_2F_5$ | H | O |
| 17 | Br | H | $OCF_2H$ | H | S | H | H | $C_2F_5$ | H | O |
| 18 | Cl | H | $CF_3$ | H | S | H | $CH_3$ | $CF_3$ | H | O |
| 19 | Cl | H | $CF_3$ | H | S | $CH_3$ | H | $CF_3$ | H | S |
| 20 | Cl | H | $CF_3$ | H | O | $CH_3$ | $CH_3$ | $CF_3$ | H | O |
| 21 | Cl | H | $CF_3$ | H | S | $CH_3$ | $CH_3$ | $CF_3$ | H | O |
| 22 | Cl | H | $CF_3$ | H | O | $CH_3$ | $CH_3$ | $C_2F_5$ | H | O |
| 23 | Cl | H | $CF_3$ | H | S | $CH_3$ | $CH_3$ | $C_2F_5$ | H | O |
| 24 | Cl | H | $CF_3$ | H | S | H | H | $CF_3$ | H | S |
| 25 | Br | H | $OCF_3$ | H | S | H | H | $CF_3$ | H | O |
| 26 | F | H | $OCF_3$ | H | S | H | H | $CF_3$ | H | O |
| 27 | Cl | H | $OCF_3$ | H | S | H | H | $C_2F_5$ | H | O |
| 28 | F | H | $OCF_3$ | H | S | H | H | $C_2F_5$ | H | O |
| 29 | Cl | H | $CF_3$ | H | O | H | H | $CH_3$ | $CF_3$ | H | O |

Also to be considered as being specifically disclosed in Table I are compounds corresponding to Compound Nos 5 to 17 and 24 to 28 wherein X is S in place of O. Also to be considered as being specifically disclosed in Table I are compounds corresponding to Compound Nos 1 and 2, 4 to 17, 20–23 and 25 to 29 wherein $R^{10}$ is S in place of O.

Examples of compounds of formula (I) wherein $R^1$ is a group of sub-formula (a') are set out in Table II.

TABLE II

| COMPOUND NO. | $R^2$ | $R^3$ | $R^4$ | $R^5$ | X | $Y^1$ | $Y^2$ | $R^{21}$ | $R^{22}$ | $R^{23}$ |
|---|---|---|---|---|---|---|---|---|---|---|
| 30 | Cl | H | $CF_3$ | H | S | H | H | H | $CF_3$ | H |
| 31 | Cl | H | $CF_3$ | H | S | H | H | $CF_3$ | H | $NO_2$ |
| 32 | Cl | H | $CF_3$ | H | S | H | H | Br | $CF_3$ | H |
| 33 | Cl | H | $CF_3$ | H | S | H | H | $CF_3$ | H | Br |
| 34 | Cl | H | $CF_3$ | H | O | H | H | H | $CF_3$ | H |
| 35 | Cl | H | $CF_3$ | H | O | H | H | $CF_3$ | H | $NO_2$ |
| 36 | Cl | H | $CF_3$ | H | O | H | H | Br | $CF_3$ | H |
| 37 | Cl | H | $CF_3$ | H | O | H | H | $CF_3$ | H | Br |
| 38 | Cl | H | $CF_3$ | H | S | $CH_3$ | H | H | $CF_3$ | H |
| 39 | Cl | H | $CF_3$ | H | S | H | $CH_3$ | $CF_3$ | H | $NO_2$ |
| 40 | Cl | H | $CF_3$ | H | S | $CH_3$ | H | Br | $CF_3$ | H |
| 41 | Cl | H | $CF_3$ | H | S | $CH_3$ | H | $CF_3$ | H | Br |
| 42 | Cl | H | $CF_3$ | H | S | $CH_3$ | $CH_3$ | H | $CF_3$ | H |
| 43 | Cl | H | $CF_3$ | H | S | $CH_3$ | $CH_3$ | $CF_3$ | H | $NO_2$ |
| 44 | Cl | H | $CF_3$ | H | S | $CH_3$ | $CH_3$ | Br | $CF_3$ | H |
| 45 | Cl | H | $CF_3$ | H | S | $CH_3$ | $CH_3$ | $CF_3$ | H | Br |

Also to be considered as being specifically disclosed in Table II are compounds corresponding to Nos 38 to 45 wherein X is O in place of S.

Examples of compounds of formula (I) wherein $R^1$ is a group of sub-formula (e') are set out in Table III.

TABLE III

| COMPOUND NO. | $R^2$ | $R^3$ | $R^4$ | $R^5$ | X | $Y^1$ | $Y^2$ | $R^{33}$ | $R^{34}$ |
|---|---|---|---|---|---|---|---|---|---|
| 46 | Cl | H | $CF_3$ | H | S | H | H | $C(CH_3)_3$ | $N(C_2H_5)_2$ |
| 47 | Cl | H | $CF_3$ | H | S | $CH_3$ | H | $C(CH_3)_3$ | $N(C_2H_5)_2$ |
| 48 | Cl | H | $CF_3$ | H | S | $CH_3$ | $CH_3$ | $C(CH_3)_3$ | $N(C_2H_5)_2$ |
| 49 | Cl | H | $CF_3$ | H | O | H | H | $C(CH_3)_3$ | $N(C_2H_5)_2$ |
| 50 | Cl | H | $CF_3$ | H | O | $CH_3$ | H | $C(CH_3)_3$ | $N(C_2H_5)_2$ |
| 51 | Cl | H | $CF_3$ | H | O | $CH_3$ | $CH_3$ | $C(CH_3)_3$ | $N(C_2H_5)_2$ |

Also to be considered as specifically disclosed in Table III are compounds corresponding to Nos 46 to 51 in which $R^{34}$ is $NH_2$ in place of $N(C_2H_5)_2$.

Examples of compounds of formula (I) wherein $R^1$ is a group of sub-formula (c') are set out in Table IV.

TABLE IV

| COMPOUND NO. | $R^2$ | $R^3$ | $R^4$ | $R^5$ | X | $Y^1$ | $Y^2$ | $R^{27}$ | $R^{28}$ |
|---|---|---|---|---|---|---|---|---|---|
| 52 | Cl | H | $CF_3$ | H | S | H | H | $N(CH_3)_3$ | $SCF_3$ |
| 53 | Cl | H | $CF_3$ | H | S | $CH_3$ | H | $N(CH_3)_3$ | $CF_3$ |
| 54 | Cl | H | $CF_3$ | H | S | $CH_3$ | $CH_3$ | $N(CH_3)_3$ | $CF_3$ |
| 55 | Cl | H | $CF_3$ | H | O | H | H | $N(CH_3)_3$ | $CF_3$ |
| 56 | Cl | H | $CF_3$ | H | O | $CH_3$ | H | $N(CH_3)_3$ | $CF_3$ |
| 57 | Cl | H | $CF_3$ | H | O | $CH_3$ | $CH_3$ | $N(CH_3)_3$ | $CF_3$ |
| 58 | Cl | H | H | H | S | H | H | H | $SOCF_3$ |
| 59 | Cl | H | H | H | S | H | H | CH | $SOCF_3$ |
| 60 | Cl | H | H | H | S | H | H | H | $SCF_3$ |
| 61 | Cl | H | H | H | S | H | H | CN | $SCF_3$ |

Compounds of formula (I) can be prepared by reacting a compound of formula (II), wherein $R^2$, $R^3$, $R^4$ and $R^5$ are as defined in relation to formula (I) and $R^{36}$ is a leaving group; with a compound of formula (III), wherein $R^1$ is as defined in relation to formula (I) and thereafter if desired (a) converting a group $R^2$-$R^5$ to a different such group, and/or (b) converting a substituent on the group $R^1$ to a different substituent. $R^{36}$ is suitably fluorine, chlorine, bromine, trifluoromethylsulphonyloxy or methanesulphonyloxy.

The reaction is suitably carried out in the presence of a solvent and a base. The base may be for example an alkali metal hydride, an alkali metal alkoxide or an alkali metal carbonate, and the solvent may be a hydrocarbon solvent, such as petroleum ether, toluene, an alcohol, an ether, such as tetrahydrofuran, or an aprotic polar solvent such as dimethylformamide or dimethylacetamide.

If necessary an appropriate catalyst such as a crown ether, alkali metal fluoride or copper can be added depending upon the precise nature of $R^{36}$.

Preferably, however, compounds of formula (I) are prepared by conversion of the cyano group in a compound of formula (A) into the group —CX—$NY^1Y^2$. Thus hydrolysis of the compound of formula (A), for example by treatment with concentrated aqueous acid, optionally containing a small proportion of water, gives the corresponding compound of formula (I) wherein X is O and $Y^1$ and $Y^2$ are both hydrogen.

Treatment of the compound of formula (A) with a compound of formula alkyl-CS-$NH_2$, for example thioacetamide, gives the corresponding compound of formula (I) wherein X is S and $Y^1$ and $Y^2$ are hydrogen. The reaction suitably takes place in the presence of dry gaseous hydrochloric acid following the process described in J.A.C.S. (1960) 82 2656 (Taylor and Zoltewicz). A suitable solvent for the reaction is dimethylformamide.

Compounds of formula (I) wherein $Y^1$ and $Y^2$ are other than hydrogen may be conveniently prepared from the corresponding compound of formula (I) wherein both $Y^1$ and $Y^2$ are hydrogen. A suitable reaction scheme is shown as Scheme 1, in the FORMULAE section below.

The dehydrating agent used in step (b) of scheme 1 is suitably a carbodiimide dehydrating agent, for example dicyclohexylcarbodiimide or N-dimethylaminopropyl-N'-ethyl-carbodiimide (preferably as its salt with hydrochloric acid).

Compounds wherein X is S may also be prepared from the corresponding compound wherein X is O, for example by treatment with Lawessons reagent or by chlorination and subsequent treatment with hydrogen sulphide as shown in Scheme 2 in the FORMULAE section when $Y^1$ and $Y^2$ are both alkyl.

The final product may be converted into a corresponding compound in which X is S=O by oxidation, for example using hydrogen peroxide or m-chloroperbenzoic acid.

When $Y^1$ is hydrogen, a similar reaction may be used, but the product of step (a) is no longer the amine salt as shown in Scheme 2.

The final product may be converted into a corresponding compound in which X is S=O by oxidation, for example using hydrogen peroxide or m-chloroperbenzoic acid.

Compounds wherein at least one of $Y^1$ and $Y^2$ is other than hydrogen may also be prepared from the corresponding acid (IV) which may be convered to the acid chloride, for example by reaction with thionyl chloride, and then reacted with an amine $NHY^1Y^2$. When $Y^1$ and $Y^2$ are both other than hydrogen, the product is the corresponding compound of formula (I). When $R^1$ is a group of formula (b') and one of $Y^1$ and $Y^2$ is hydrogen, for example when the acid chloride (V) is reacted with $CH_3NH_2$, opening of the pyrimidinone ring may take place to give a compound of formula (VI). However, reaction of this product with a ring closing agent, for example a Vilsmeir Haack reagent such as that derived from phosphorous oxychloride and dimethylformamide then gives the corresponding compound of formula (I).

Compounds of formula (A) above can be prepared as described in EP O 398 499 which also lists examples of compounds of formula (A) suitable for conversion into compounds of the present invention.

Thus Examples of compounds of formula (A) wherein $R^1$ is a group of sub-formula (b') are listed in Table I of EP O 398 499. When $R^2$ in Table I of EP O 398 499 is also —CN, both cyano groups may undergo conversion to give a compound of formula (I) wherein $R^2$ is a group $—CX—NY^1Y^2$.

Examples of compounds of formula (A) wherein $R^1$ is a group of sub-formula (a') as defined above are set out in Table II of EP O 398 499. Examples of compounds of formula (A) wherein $R^1$ is a group of sub-formula (e') as defined above are set out in Table III of EP O 398 499. Examples of compounds of formula (A) wherein $R^1$ is a group of sub-formula (c') as defined above are set out in Table IV of EP 0398 499.

Conversion of a group $R^2$-$R^5$ to a different such group or converting a substituent on $R^1$ to a different substituent may be carried out by conventional methods such as described for example in EP O 398 499.

The conversion of groups $R^2$-$R^5$ to different such groups may be carried out on the compound of formula (II) prior to coupling with the compound of formula (III), if desired. The methods for a conversion of this type is suitably the same as described above in relation to the equivalent conversions on the compounds of formula (I) or (A). Further examples of suitable interconversion reactions are given in the Preparations below and include for example; i) the conversion of a nitro group into a halogen group; ii) the conversion of a nitro group into an amino group and subsequent conversion of the amino group into a halogen group; and iii) the conversion of a halogen group into a cyano group.

The compounds of formula (I) may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of solid preparations that may be applied diluted or undiluted.

Solid compositions that may be applied undiluted may be in the form of dusting powders wherein the active ingredient is mixed with a solid diluent or carrier, eg kaolin, bentonite, kieselguhr, silica or talc. Or the solid composition may be in the form of granules wherein the active ingredient is absorbed on a non-porous granular material, for example, calcium carbonate, or may be impregnated in a porous granular material, for example, pumice or gypsum.

Solid compositions that may be applied diluted may be in the form of wettable powders wherein the active ingredient is mixed with a solid diluent or carrier, such as kaolin, kieselguhr or silica and appropriate surface acting agents or they may be in the form of water dispersible granules, wherein the active ingredient is mixed with a solid diluent or carrier, for example, kaolin, kieselguhr or silica and an appropriate surface acting agent, and then granulated.

Alternatively, the compositions may be in the form of liquid preparations to be used as dips, sprays or aerosol dispersions or non-aqueous solutions of the active ingredient and are usually diluted before application.

Aqueous dispersions of the active ingredient which may be applied diluted may be in the form of suspension concentrates wherein the active ingredient is dispersed in an aqueous media. These compositions contain dispersing/wetting agents and one or more stabilizing agents, for example, bentonite clays and/or polysaccharide gels. Additional further components may be included such as antifreeze agents, for example, ethylene glycol, propylene glycol or salts, and biocides, for example, Proxel GXL (1,2-benzisothiazolin-3-one).

Other aqueous dispersions of the active ingredient may be in the form of microcapsule suspensions wherein the active ingredient is encapsulated, as a high strength water immiscible solution, with a polymer and the subsequent microcapsules are dispersed in aqueous media. The microencapsulation technique used may be of the type described in the patent literature. These compositions contain dispersing/wetting agents and one or more stabilizing agents, for example, bentonite clays and/or polysaccharide gels. Additional further components may be included such as anti-freeze agents and biocides as previously described.

Other aqueous dispersions of the active ingredient may be in the form of oil in water emulsions wherein the active ingredient is dissolved in a suitable solvent, for example, an aromatic hydrocarbon such as trimethylbenzene or a ketonic solvent such as di-hydroisophorone alone with one or more emulsifying agents and then emulsifying the solution so obtained into water which may contain further surface active agents. Other suitable organic solvents are ethylene dichloride, toluene, kerosene, white oil, methylnapthalene, xylenes, trichloroethylene, vegetable oils, N-methyl-2-pyrrolidone and isophorone.

Alternatively liquid compositions may be in the form of non-aqueous solutions to be used diluted or undiluted as sprays or aerosol fogs.

Non-aqueous preparations that may be applied undiluted may be in the form of low volume or ultra low volume concentrates wherein the active ingredient is dissolved in a suitable solvent or mixture of solvents, for example, an aromatic hydrocarbon such as trimethylbenzene or aliphatic hydrocarbon such as kerosene. Other suitable solvents are isophorone, di-hydroisophorone, toluene, xylenes, methylnapthalenes, N-methylpyrrolidone, mineral oil and vegetable oils. These preparations are optionally diluted before application with paraffinic solvents, such as diesel oil.

Other non-aqueous preparations may be in the form of emulsifiable concentrates wherein the active ingredient is dissolved in a suitable solvent, for example, trimethyl- benzenes or methylcyclohexanone, with one or more emulsifying agents. Other suitable solvents are as previously described. These preparations are diluted in water to form aqueous dispersions before application.

Further formulation types may include preparations for special use such as aerosols wherein the composition will contain the active ingredient or ingredients, a propellant and an inert diluent, for example, odourless kerosenes or alkylated benzenes. In a preferred form, aerosol compositions may contain from 0.005% to 4% of active ingredient or ingredients, the remainder of the composition may be aqueous based in which an aqueous component is dispersed in a solution of active ingredient in a solvent, such as previously described, and a propellant by using one or more surface active agents. Aerosol compositions may optionally incorporate other additives, for example, knockdown agents, synergists, perfumes and corrosion inhibitors.

Other formulations for special purposes may be in the form of ready for use sprays wherein the active ingredient is dissolved in a solvent, for example, odourless kerosenes and alkylated benzenes and applied through a hard pump device to be used as a residual spray. These compositions may optionally incorporate other additives such as knockdown agents, synergists and perfumes.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10-85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient (approximately equivalent to from 5-2000 g/ha) is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of the invention may be the sole active ingredient of the composition or they may be admixed with one or more additional active ingredients such as insecticides, insecticide synergists, herbicides, fungicides or plant growth regulators where appropriate. Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

a) Pyrethroids such as permethrin, esfenvalerate, deltamethrin, cyhalothrin in particular lambda- cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)-cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, chloropyrifos, phosalone, fensulfothion, fonofos, phorate, phoxim, pyrimiphos-methyl, fenitrothion or diazionon;

c) Carbamates (including aryl carbamates) such as pirimicarb, cloethocarb, carbofuran, ethiofencarb, aldicarb, thiofurox, carbosulan, beniocarb, fenobucarb, propoxur or oxamyl;

d) Benzoyl ureas such as triflumeron, or chlorofluazuron;

e) Organic tin compounds such as cyhexatin, fenbutatin oxide, azocyclotin;

f) Macrolides such as avermectins or milbemyins, for example such as abamectin, avermectin, and milbemycin;

g) Hormones such as pheromones;

h) Organochlorine compounds such as benzene hexachloride, DDT, chlordane or dieldrin.

i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as clofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S.

The ratio of the compound of the invention to the other active ingredient in the composition will depend upon a number of factors including type of target, effect required from the mixture etc.

However in general, the additional active ingredient of the composition will be applied at about the rate as it is usually employed, or at a slightly lower rate if synergism occurs.

The compounds of formula I and compositions comprising them have shown themselves active against a variety of insect and other invertebrate pests. They are particularly useful in controlling public health pests such as flies and cockroaches. They may also be active against organophosphate and pyrethroid resistant strains of pests such as houseflies (*Musca domestica*). They may be effective in combating both susceptible and resistant strains of the pests in their adult, larval and intermediate stages of growth, and may be applied to the infested host animal by topical, oral or parenteral administration.

The following Preparations and Examples illustrate various aspects of the invention. In the Preparations and Examples the compounds were identified and characterised by means of the melting points, nuclear magnetic resonance spectroscopy (in $CDCl_3$ or $d^6DMSO$, using a Jeol GSX machine at 270 mHz), mass spectroscopy (using a VG TRIO 1 machine) or infra red spectroscopy (using a Perkin-Elmer Model 881).

According to a further aspect of the present invention there is provided novel intermediates exemplified in Preparations 1 to 14.

Preparation 1

This description illustrates the preparation of 4-chloro-3-cyano-5-nitrotrifluoromethoxybenzene.

Step 1

2-Nitro-4-trifluoromethoxyaniline was converted into 2-bromo-6-nitro-4-trifluoromethoxyaniline using the general procedure illustrated in Preparation 8 (step a) below. The material was immediately carried through to step 2.

Step 2

2-Bromo-6-nitro-4-trifluoromethoxyaniline was converted into 2-cyano-6-nitro-4-trifluoromethoxyaniline using the general method illustrated in Example 6 (of EP 0 398 499). In such Example, a mixture of 1-(2-bromo-6-fluoro-4-trifluoromethylphenyl)-4-trifluoromethylpyrimidin-6-one (0.15 g), copper (I) cyanide (36 mg) and copper (I) iodide (76 mg) in dry N-methylpyrrolidinone (2 ml) was heated to 160° C. for 16 hours. On cooling to ambient temperature the reaction mixture was poured into water and extracted with ethyl acetate. The organic extracts were washed with water and brine, and dried over anhydrous magnesium sulphate. Evaporation of the solvent under reduced pressure gave a brown oil which was then subjected to Kugelrohr distillation under reduced pressure (120° C., 15 mmHg approx) to remove residual N-methylpyrrolidinone. The residue was subjected to medium pressure liquid chromatography on a Gilson apparatus using silica gel as the stationary phase and eluting with hexane containing ethyl acetate (5% by volume). The appropriate fractions were collected to give 1-(2-cyano-6-fluoro-4-trifluoromethylphenyl)-4-trifluoromethylpyrimidin-6-one as a pale yellow solid. The 2-cyano-6-nitro-4-trifluoromethoxyaniline was immediately carried through to step 3.

Step 3

2-Cyano-6-nitro-4-trifluoromethoxyaniline was converted into 4-chloro-3-cyano-5-nitrotrifluoromethoxybenzene using the general method illustrated in Preparation 5 of EP 0 398 499. In such Preparation, 4-amino-3-chloro-5-cyano-trifluoromethylbenzene (5.1 g) in dry acetonitrile (0.25 ml) was added dropwise to a stirred suspension of copper (II) chloride (3.72 g) and tertiary butyl nitrite (12.24 g) in dry acetonitrile (75 ml) whilst the temperature was maintained between 0° and +5° C. After the addition was complete, stirring was continued for a further 2 hours, whereupon the reaction mixture was diluted with dilute aqueous hydrochloric acid, and extracted with ethyl acetate. The organic layer was washed with water, and after drying over anhydrous magnesium sulphate, evaporation of the solvent under reduced pressure gave an orange oil which crystallised on standing. Kugelrohr distillation gave 3-cyano-4,5-dichloro-trifluoromethylbenzene as a pale yellow oil which crystallised on standing.

Preparation 2

This description illustrates the preparation of 1-(2-bromo-6-chloro-4-[1',1',2',2'-tetrafluoroethoxy]-phenyl)-4-trifluoromethylpyrimidin-6-one.

Step 1

4-Nitro-(1',1',2',2'-tetrafluoroethoxy-benzene was converted to 4-(1',1',2',2'-tetrafluoroethoxy)-aniline using the general procedure illustrated in Preparation 12 of EP 0 398 499. In such Preparation, reduced iron powder (0.18 g) was added to a suspension of 1-(2-fluoro-6-nitro-4-trifluoromethylphenyl)-4-trifluoromethylpyrimidin-6-one (0.6 g) in a mixture of isopropanol (6 ml) and water (0.6 ml). Concentrated hydrochloric acid (1 drop) was added, and the reaction mixture was heated to 100° C. for a period of 5 hours. After cooling to ambient temperature, the reaction mixture was filtered through celite, and the residue washed with ethyl acetate. Evaporation of the filtrate under reduced pressure gave 1-(2-amino-6-fluoro-4-trifluoromethylphenyl)-4-trifluoromethylpyrimidin-6-one.

The product was immediately carried on to step 2.

Step 2

Acetic anhydride (32.2 mls) was added dropwise to a solution of 4-(1',1',2',2'-tetrafluoroethoxy)-aniline (step 1) (70 g) in acetic acid (140 mls). The reaction temperature rose to 50° C. After stirring for 1 hour, the reaction mixture was poured onto ice, and the solid so formed was collected at the pump. The solid was dissolved in dichloromethane and carefully dried. Removal of the solvent by evaporation under reduced pressure gave 4-(1',1',2',2'-tetrafluoroethoxy)-acetamide as a solid. Melting Point: 96.3°-97.4° C.

Step 3

Fuming nitric acid (75 mls) was added dropwise to a stirred suspension of 4-(1',1',2',2'-tetrafluoroethoxy)-acetamide (step 2) (75 g) in dichloromethane (700 mls). After stirring overnight, the reaction mixture was poured into ice, and the so generated mixture made slightly basic with aqueous sodium carbonate solution. The mixture was then extracted with dichloromethane, and the combined organic extracts washed with water and dried over anhydrous magnesium sulphate. Removal of the solvent by evaporation under reduced pressure gave 2-nitro-4-(1',1',2',2',-tetrafluoroethoxy)-acetamide as a bright yellow solid.
Melting Point: 73.5°-74.5° C.

Step 4

2-Nitro-4-(1',1',2',2'-tetrafluoroethoxy)-acetamide (step 3) (94 g) was dissolved in methanol (680 mls). An aqueous solution of sodium hydroxide (6M) (160 mls) was then added dropwise. The reaction mixture was then stirred for 1 hour, at which point it was cooled in an ice bath, and water (1300 mls) was slowly added. The whole was then poured into ice and the yellow precipitate so formed was collected at the pump and water-washed to give 2-nitro-4-(1',1',2',2'-tetrafluoroethoxy)-aniline as a bright orange solid. Melting Point: 83.9°-84.4° C.

Step 5

30% Hydrogen peroxide (46 ml) was added dropwise to a cooled solution of 2-nitro-4-(1',1',2',2'-tetrafluoromethoxy)-aniline (step 4) (20 g) in concentrated hydrochloric (150 mls). A small exotherm was noted. After the addition was complete, stirring was continued for a further hour, whereupon the reaction mixture was poured into water, and made basic with 2M aqueous sodium hydroxide (with ice cooling). Extraction with ethyl acetate, followed by water washing as the combined aqueous extracts, drying over anhydrous magnesium sulphate and removal of the solvent by evaporation under reduced pressure give 2-chloro-6-nitro-4-(1',1',2',2'-tetrafluoromethoxy)-aniline as a brown solid.
$^1$H NMR δ(COCl$_3$): 8.00(1H,d), 7.58(1H,d), 6.60(2H,broad s), 5.91(1H,tt).

Step 6

2-Chloro-6-nitro-4-(1',1',2',2'-tetrafluoroethoxy)-aniline (step 5) (10 g) was converted into 3,4-dichloro-5-nitro-(1',1',2',2'-tetrafluoroethoxy) -benzene using the general procedure, illustrated in Preparation 5 of EP 0 398 499(see Preparation 1, Step 3, above). $^1$H NMR δ(CDCl$_3$): 7.62(2H,s), 5.97(1H,s).

Step 7

3,4-Dichloro-5-nitro-(1',1',2',2'-tetrafluoroethoxy)-benzene (6.4 g) was added to a pre-dried solution of caesium fluoride (4.9 g) and sulpholane (70 ml). The stirred reaction mixture was then heated to 110° C. for a total of 27 hours. After allowing to cool to the ambient temperature, the reaction mixture was diluted with water and poured into hexane. The organic layer was water washed, dried over anhydrous magnesium sulphate, and the solvent removed by evaporation under reduced pressure to give 3-chloro-4-fluoro-5-nitro-(1',1',2', 2'-tetrafluoroethoxy)-benzene as an orange oil.
$^1$H NMR δ(CDCl$_3$): 7.85(1H,m), 7.62(1H,m), 5.95(1H,tt).

Step 8

A solution of 4-trifluoromethylpyrimidin-6-one (2.8 g), and N,N-disopropylethylamine (2.5 mls) was stirred in dry N-methylpyrrolidinone (10 mls) for a period of 30 minutes. A solution for 3-chloro-4-fluoro-5-nitro-(1',1',2',2'-tetrafluoroethoxy)-benzene (4.0 g) (step 7) in dry N-methylpyrrolidinone (10 mls) was then added portion-wise, and the stirred reaction mixture was heated to 80° C. for 1 hour. After allowing to cool to ambient temperature, the reaction mixture was poured into water and extracted into diethyl ether. The combined organic extracts were water washed, dried over anhydrous magnesium sulphate, and concentrated by evaporation of the solvent under reduced pressure to give an orange solid. Silica column chromatography using hexane containing ethyl acetate (13% by volume) gave 1-(2-chloro-6-nitro-4-[1',1',2',2'-tetrafluoroethoxy]-phenyl)-4-trifluoromethylpyrimidin-6-one as a pale yellow solid. This material was immediately carried through to stage 9.

Step 9

1-(2-chloro-6-nitro-4-[1',1',2',2'-tetrafluoroethoxy]-phenyl)-4-trifluoromethylpymidin-6-one (step 8) was converted to 1-(2-amino-6-chloro-4-[1',1',2',2'-tetrafluoroethoxy]-phenyl)-4-trifluoromethylpyrimidin-6-one using the general method illustrated in Preparation 12 of EP 0 398 499 (see Preparation 2, Step 1, above). $^1$H NMR δ(CDCl$_3$): 8.05(1H,s), 6.95(1H,s), 6.72(1H,s), 6.71(1H,s), 6.02(1H,tt), 5.17(1H,broad s).

Stage 10

1-(2-amino-6-chloro-4-[1',1',2',2'-tetrafluoroethoxy]-phenyl)-4-trifluoromethylpyrimidin-6-one was converted to 1-(2-bromo-6-chloro-4-[1',1',2',2'-tetrafluoroethoxy]-phenyl)-4-trifluoromethylpyrimidin-6-one using the general method illustrated in Preparation 5 of EP 0 398 499 (see Preparation 1, Step 3, above). In this example copper (II) bromide was used instead of copper (II) chloride as the halide source. Melting Point: 123.8°-124.5° C.

Preparation 3

The following preparations were undertaken using the general method of Example 2 of EP 0 398 499. This Example involved the preparation of compounds employing the general method of producing 1-(2-cyano-4-trifluoromethylphenyl)-4-trifluoromethylpyrimidin-6-one as follows: A dry reaction flask was purged with nitrogen and charged with 50% sodium hydride (0.16 g). The solution hydride was washed with petroleum ether (boiling range: 60°-80° C.) and suspended in dry dimethylformamide (DMF, 10 ml). 4-Trifluoromethyl-pyrimidin-6-one (0.5 g) was added portionwise, and when the addition was complete the reaction was stirred for a further 30 minutes. 3-Cyano-4-fluoro-trifluoromethylbenzene (1.13 g) was added, and the reaction mixture was heated to 80° C. for 16 hours. The reaction mixture was allowed to cool, poured into water, and extracted with ethyl acetate. The organic layer was washed with brine, dried over anhydrous magnesium sulphate and evaporated under reduced pressure to give a brown oil which solidified. The solid was flushed through a plug of silica using petroleum ether (boiling range 60°-80° C.) containing diethyl ether (20% by volume) as eluent. Evaporation of the solvent, under reduced pressure, gave a pale brown solid which was triturated with petroleum ether (boiling range: 60°-80° C.) to give an off-white solid, which was then recrystallised from petroleum ether (boiling range: 60°-80° C.) containing diethylether (33% by volume).

a) 1-(2-Chloro-6-cyano-4-trifluoromethylphenyl)-5-methyl-4-trifluoromethylpyrimidin-6-one was prepared by the reaction of the product of Preparation 2 of EP 0 398 499 (i.e., 3-chloro-4-fluoro-5-cyano-trifluoromethylbenzene, produced as follows: A solution of 3-amino-5-chloro-4-fluorotrifluoromethylbenzene (3 g) in acetonitrile (10 ml) was added dropwise to a stirred suspension of copper (I) cyanide (1.26 g) in dry acetonitrile (50 ml) whilst the reaction temperature was maintained at 0° C. After the addition was complete, the reaction mixture was allowed to warm to the ambient temperature (about 23° C.) and left overnight. The reaction mixture was poured into water, extracted with diethyl ether, dried over anhydrous magnesium sulphate and filtered. Evaporation of the solvent, under reduced pressure, gave a brown oil, which was flushed through a plug of silica gel using petroleum ether (boiling range 60°-80° C.) containing diethyl ether (20% by volume) as eluent. After removal of the solvent, under reduced pressure, Kugelrohr distillation of the residue gave two fractions, the first of which (boiling point 110° C. at 15 mmHg) was predominantly composed of 3-chloro-4-fluoro-5-cyano-trifluoromethylbenzene and 5-methyl-4-trifluoromethylpyrimidin-6-one. The product had a melting point of 154.1°-154.9° C.

5-methyl-4-trifluoromethylpyrimidin-6-one was prepared as follows:-

Stage 1

Thiourea (14.36 g) was added to a solution of sodium methoxide in methanol (previously prepared by adding sodium metal (3.34 g) to dry methanol (61.5 ml)). This was followed by ethyl-2-methyl-4,4,4-trifluoroacetoacetate (25 g) and the reaction mixture was heated under reflux for 66 hours. After cooling to ambient temperature, the solvent was evaporated under reduced pressure to give a brown solid, which was then acidified with dilute aqueous hydrochloric acid and extracted with diethyl ether.

The combined organic extracts were dried, and subsequent removal of the solvent by evaporation under reduced pressure to give a brown residue. This was triturated with a small amount of diethyl ether in hexane to give 5-methyl-4-trifluoromethyl-2-thiouracil.

$^1$H NMR $\delta(d^6DMSO)$ 12.80 (2H, broad s); 1.88 (3H,m).

Stage 2

Raney Nickel (3.45 g of a 50% dispersion in water) was added to a suspension of 5-methyl-4-trifluoromethyl-2-thiouracil (2 g; Stage 1) in a mixture of concentrated aqueous ammonia (0.96 ml) in water (25 ml). The reaction was heated to reflux for 4.5 hours and filtered hot through celite. The filtrate was concentrated by evaporation of the solvent under reduced pressure to give the desired compound as a pale green solid. Sublimation (130° C. at 0.07 mmHg) gave 5-methyl-4-trifluoromethylpyrimidin-6-one as a pale green solid of melting point 174.9°-176.4° C. $^1$H NMR $\delta(CDCl_3)$ 8.15 (1H, s); 2.25 (3H,m).

b) 1-(2-Bromo-6-cyano-4-trifluoromethylphenyl)-5-methyl-4-pentafluoroethylpyrimidin-6-one was prepared by the reaction of 3-bromo-4-fluoro-5-cyano-trifluoromethylbenzene (Preparation 8 of EP 0 398 499;) produced by employing 3-bromo-4-chloro-5-cyanotrifluoromethylbenzene as a reactant using the following general method employed to produce 3-chloro-4-fluoro-5-cyano-trifluoromethylbenzene:

Dry potassium fluoride (1.94 g) was added to a flash containing dry toluene (31 ml), dry dimethylformamide (7.8 ml) and a catalytic amount of 18-crown-6. The stirred mixture was heated to reflux, and approximately 25 mls of the distillate was collected. After cooling to ambient temperature, 3-cyano-4,5-dichloro-trifluoromethylbenzene (4 g) was added in one portion, and the stirred mixture was heated at 130° C. for 16 hours, and then to 145° C. for 24 hours. After cooling to ambient temperature, the reaction mixture was filtered, the residue washed with ethyl acetate, and the combined filtrate washed with brine. After drying over anhydrous magnesium sulphate, evaporation under reduced pressure gave a brown oil which was subjected to Kugelrohr distillation, to give 3-chloro-4-fluoro-5-cyano-trifluoromethylbenzene as a pale yellow liquid (3.17 g). and 5-methyl-4-pentafluoroethylpyrimidin-6-one. The product had a melting point of 150.2°-151.8° C.

5-Methyl-4-pentafluoroethylpyrimidin-6-one was prepared as follows:

A dry reaction flask was purged with nitrogen and charged with 55% sodium hydride in oil (0.82 g). The sodium hydride was washed with hexane and suspended in dry tetrahydrofuran (80 ml). 5-bromo-4-pentafluoroethylpyrimidin-6-one (5 g) was added portionwise, and when the addition was complete the reaction was stirred for a further 30 minutes. A solution of tertiary butyl lithium (221 ml of a 1.7M solution in pentane) was then added dropwise to the cooled (−78° C.) reaction mixture, whilst ensuring that the temperature was maintained below −60° C. The reaction mixture was then stirred for a further hour, whereupon methyl iodide (10.6 ml) was added in one portion. The temperature of the reaction mixture was allowed to rise to −10° C. in steps over a period of 4½ hours and the reaction mixture was then poured into 2M aqueous hydrochloric acid (300 ml), and extracted with ethyl acetate. The combined aqueous extracts were washed with saturated aqueous sodium metabisulphite, followed by brine, and then dried, filtered and concentrated by evaporation of the solvent under reduced pressure to give a buff coloured solid. Tituration with hexane, followed by recrystallisation from toluene, gave the desired product as an off-white solid: Melting point: 145.4°-146.8° C.; $^1$H NMR $\delta(CDCl_3)$ 8.19 (1H,s); 2.3 (3H,t).

c) 1-(2-chloro-6-cyano-4-trifluoromethylphenyl)-5-methyl-4-pentafluoroethylpyrimidin-6-one was prepared from the product of Preparation 2 of EP 0 398 499 (see Preparation 3a, above) and 5-methyl-4-pentafluoroethylpyrimidin-6-one:

Melting Point: 158.0°-159.6° C.

Preparation 4

This description illustrates the preparation of 1-(2-Cyano-6-nitro-4-trifluoromethylphenyl)-5-methyl-4-pentafluoroethylpyrimidin-6-one.

A solution of 5-methyl-4-pentafluoroethylpyrimidin-6-one (see Preparation 3) (1.0 g) was added to a solution of potassium t-butoxide (0.5 g) in dry diglyme (5 mls).

After stirring for a period of 30 minutes, a solution of 4-chloro-3-cyano-5-nitro-trifluormethylbenzene (see Example 2f of EP 0 398 499 1-(2-Cyano-6-nitro-4-trifluoromethylphenyl)-4-trifluoromethylpyrimidin-6-one prepared by the reaction of 4-chloro-3-cyano-5-nitrotrifluoromethylbenzene and 4-trifluoromethylpyrimidin-6-one as generally described in Preparation 3 above) (11.2 g) in dry diglyme (5 mls) was added dropwise. After stirring for a further 2 hours, at the ambient temperature, the reaction mixture was slowly added to water (50 mls) containing Synperonic NP13 while stirring vigourously. The resultant yellow precipitate was collected at the pump. Trituration with hexane containing ethyl acetate (10% by volume) gave the desired product as an off-white solid. Melting Point: 213°–214° C.

Preparation 5

The following compounds were made according to the general method illustrated in Preparation 4.
a) 1-(2-Cyano-6-nitro-4-trifluoromethylphenyl)-5-methyl-4-trifluoromethylpyrimidin-6-one from 5-methyl-4-trifluoromethylpyrimidin-6-one (see preparation 3) and 4-chloro-3-cyano-5-nitrotrifluoromethylbenzene. Melting Point: 178°–179° C.
b) 1-(2-Cyano-6-nitro-4-trifluoromethoxyphenyl)-4-trifluoromethylpyrimidin-6-one from 4-chloro-3-cyano-5-nitro-trifluoromethoxybenzene (the product of Preparation 1) and 4-trifluoromethylpyrimidin-6-one. In the procedure the reaction mixture was heated to 95° C. for a period of 3 hours.
c) 1-(2-Cyano-4-difluoromethoxy-6-nitrophenyl)-4-pentafluoroethylpyrimidin-6-one from 4-chloro-3-cyano-5-nitro-difluoromethoxybenzene (see Preparation 8, step 3, below) and 4-pentafluoroethylpyrimidin-6-one. In this preparation the reaction mixture was heated to 90° C. for a period of 7½ hours. $^1$H NMR δ(CDCl$_3$): 8.28 (1H, d), 8.20 (1H,s), 7.92 (1H;d), 7.02 (s, 1H), 6.75 (1H,t).
d) 1-(2-Cyano-6-nitro-4-trifluoromethoxyphenyl)-4-pentafluoroethylpyrimidin-6-one from 1-(4-chloro-3-cyano-5-nitro-trifluoromethoxybenzene (the product of Preparation 1) and 4-pentafluoroethylpyrimidin-6-one. In this preparation the reaction mixture was heated to 90° C. for a period of 4 hours. $^1$H NMR δ(CDCl$_3$): 8.33 (1H,d), 8.19 (1H,s), 7.99 (1H,d), 7.04 (1H,s).

Preparation 6

An alternative procedure for the preparation of 1-(2-cyano-6-fluoro-trifluoromethylphenyl)-4-trifluoromethylpyrimidin-6-one is illustrated. 1-(2-Cyano-6-nitro-4-trifluoromethylphenyl)-4-trifluoromethylpyrimidin-6-one (the product of Example 2f of EP 0 398 499 (see Preparation 4 above)) (5.7 g) was added to a preheated (80° C.) suspension of potassium fluoride (1.6 g) in dry dimethylformamide (27 mls). The reaction temperature was then raised to 115° C. for a period of 2½ hours. After cooling to the ambient temperature, the reaction mixture was poured into water and extracted into ethyl acetate. The combined organic extracts were washed with water and brine, dried, and removal of the solvent by evaporation under reduced pressure afforded a viscous black oil. Medium pressure chromatography on a Gilson apparatus, using silica as the stationary phase, and eluting with hexane containing ethyl acetate (10% by volume) gave the desired product. $^1$H NMR δ(CDCl$_3$): 8.17(1H,s); 7.99(1H,s); 7.89(1H,d); 7.04(1H,s).

Preparation 7

The following compounds were prepared according to the general method of Preparation 6.
a) 1-(2-Cyano-6-fluoro-4-trifluoromethylphenyl)-5-methyl-4-pentafluoroethylpyrimidin-6-one from 1-(2-cyano-6-nitro-4-fluoroethylphenyl)-5-methyl-4-pentafluoroethylpyrimidin-6-one (the product of Preparation 4). $^1$H NMR δ(CDCl$_3$): 8.00 (1H,s), 7.98(1H,s), 7.88 (1H,d), 2.37(3H,t).
b) 1-(2-Cyano-6-fluoro-4-trifluoromethylphenyl)-5-methyl-4-trifluoromethylpyrimidin-6-one from 1-(2-cyano-6-nitro-trifluoromethylphenyl)-5-methyl-4-trifluoromethylpyrimidin-6-one (the product of Preparation 5a). $^1$H NMR δ(CDCl$_3$): 8.01(1H,s); 7.96 (1H,s); 7.88(1H,d); 2.36(3H,t).
c) 1-(2-Cyano-4-fluoro-6-trifluoromethoxyphenyl)-4-trifluoromethylpyrimidin-6-one from 1-(2-cyano-6-nitro-4-trifluoromethoxyphenyl)-4-trifluoromethylpyrimidin-6-one (the product of Preparation 5b). $^1$H NMR δ(CDCl$_3$): 8.17(1H,s); 7.57(1H,s); 7.52(1H,d); 7.02(1H,s).
d) 1-(2-Cyano-6-fluoro-4-trifluoromethoxyphenyl)-4-pentafluoroethyl-pyrimidin-6-one from 1-(2-cyano-6-nitro-4-trifluoromethoxy)phenyl-4-pentafluoroethylpyrimidin-6-one (the product of Preparation 5d). Melting Point: 124.8°–125.6° C.

Preparation 8

This description illustrates the preparation of 1-(2-cyano-4-difluoromethoxy-6-fluorophenyl)-4-pentafluoroethylpyrimidin-6-one.

Step 1

Bromine (10 cm$^3$) was added to a stirred suspension of 4-difluoromethoxy-2-nitroaniline (available as described for example in Example B5(b) of U.S. Pat. No. 4,686,230.) (26.6 g) and sodium acetate trihydrate (19.5 g) in carbon tetrachloride (250 mls). After stirring at ambient temperature for a period of 30 minutes, the reaction mixture was added to dichloromethane (350 mls) and washed with aqueous sodium metabisulphite solution, followed by aqueous sodium bicarbonate solution, and finally brine. The organic layer was the dried over anhydrous magnesium sulphate, and removal of the solvent by evaporation under reduced pressure, gave 6-bromo-4-difluoromethoxy-2-nitroaniline as an orange-brown solid. Melting Point: 60.5°–61.5° C. (cyclohexane).

Step 2

2-Cyano-4-difluoromethoxy-6-nitroaniline was prepared from 6-bromo-4-difluoromethoxy-2-nitroaniline (step 1) according to the general method of Example 6 of EP 0 398 499 . (In such Example, a mixture of 1-(2-bromo-6-fluoro-4-trifluoromethylphenyl-4-trifluoromethylpyrimidin-6-one (0.15 g), copper (I) cyanide (36 mg) and copper (I) iodide (76 mg) in dry N-methylpyrrolidinone (2 ml) was heated to 160° C. for 16 hours. On cooling to ambient temperature, the reaction mixture was poured into water and extracted with ethyl acetate. The organic extracts were washed with water and brine, and dried over anhydrous magnesium sulphate. Evaporation of the solvent under reduced pressure gave a brown oil which was then subjected to Kugelrohr distillation under reduced pressure (120° C., 15 mmHg approx) to remove residual N-methylpyrrolidinone. The residue was subjected to medium pressure liquid chromatography on a Gilson apparatus using silica gel as the stationary phase and eluting with hexane containing ethyl acetate (5% by volume). The appropriate fractions were collected to give 1-(2-cyano-6-fluoro-4-trifluoromethylphenyl)-4-trifluoromethylpyrimidin-6-one as a pale yellow solid.) Melting Point: 99°–100° C.

Step 3

4-Chloro-3-cyano-5-nitrofluoromethoxybenzene was prepared from 2-cyano-4-difluoromethoxy-6-nitroaniline (step 2) using the general procedure illustrated in Preparation 5 of EP 0 398 499 (see Preparation 1, Step 3, above). Melting Point: 27°–28° C.

Step 4

A mixture of 4-chloro-3-cyano-5-nitro-difluoromethoxybenzene (3.3 g), 4-pentafluoroethylpyrimidin-6-one (2.94 g), ethyl-di-isopropylamine (1.8 g), and potassium fluoride (spray dried, 2.4 g) in dry N-methyl-2-pyrrolidinone (5 cm$^3$) was stirred vigorously and heated to 130° C. for 3 hours. After allowing to cool to the ambient temperature, the reaction mixture was poured into water, and extracted with diethyl ether. The combined organic extracts were washed with water, dried over anhydrous magnesium sulphate, and removal of the solvent by evaporation under reduced pressure afforded a brown gum. Column chromatography on silica using hexane containing ethyl acetate (17% by volume) afforded the desired product. Melting Point: 101.4°–103.4° C.

Preparation 9

This description illustrates the preparation of 1-(2-chloro-6-cyano-4-trifluoromethoxyphenyl)-4-trifluoromethylpyrimidin-6-one.

Step 1

1-(2-Cyano-6-nitro-4-trifluoromethoxyphenyl)-4-trifluoromethyl-pyrimidin-6-one (the product of Preparation 5b), was converted through to 1-(2-amino-6-cyano-4-trifluoromethoxyphenyl)-4-trifluoromethylpyrimidin-6-one using the general procedure illustrated in Preparation 12 of EP 0 398 499 (see Preparation 2, Step 1, above). The material was immediately carried through onto to step 2.

Step 2

1-(2-amino-6-cyano-4-trifluoromethoxyphenyl)-4-trifluoromethyl-pyrimidin-6-one (step 1) was converted through to 1-(2-chloro-6-cyano-4-trifluoromethoxyphenyl)-4-trifluoromethylpyrimidin-6-one using the general method illustrated in Preparation 5 of EP 0 398 499 (see Preparation 1, Step 3, above). Melting Point: 132.0°–133.0° C.

Preparation 10

1-(2-Chloro-6-cyano-4-[1',1', 2',2'-tetrafluoroethoxy]-phenyl)-4-trifluoromethylpyrimidin-6-one was prepared from 1-(2-amino-6-chloro-4-[1',1',2', 2'-tetrafluoroethoxy]-phenyl)-4-trifluormethylpyrimidin-6-one (Preparation 2, Stage 9) using the general method illustrated in Preparation 6 of EP 0 398 499 (This Preparation 6 involved the conversion of 4-amino-3-bromo-5-cyano-trifluoromethyl benzene into 3-bromo-5-chloro-5-cyano-trifluoromethyl benzene using the general method of Preparation 5 of such publication. See Preparation 1, Step 3, above). $^1$H NMR δ(CDCl$_3$/d$^6$DMSO): 8.50 (1H,s); 7.85(1H,d); 7.80(1H,d); 7.03(1H,s); 6.29(1H,tt).

Preparation 11

This description illustrates the preparation of 1-(2-chloro-6-cyano-4-difluoromethoxyphenyl)-4-pentafluoroethylpyrimidin-6-one.

Step 1

1-(2-Cyano-4-difluoromethoxy-6-nitrophenyl)-4-pentafluoroethyl-pyrimidin-6-one (the product of preparation 5c) was converted to 1-(2-amino-6-cyano-4-difluoromethoxyphenyl)-4-pentrafluoroethylpyrimidin-6-one using the general procedure illustrated in Preparation 12 of EP 0 398 499 (see Preparation 2, Step 1, above). Melting Point: 171°–172.8° C.

Step 2

1-(2-Amino-6-cyano-4-difluoromethoxyphenyl)-4-pentafluoroethyl-pyrimidin-6-one (step 1) was converted to 1-(2-chloro-6-cyano-4-difluoromethoxyphenyl)-4-pentafluoroethylpyrimidin-6-one using the general procedure illustrated in Preparation 5 of EP 0 398 499 (see Preparation 1, Step 3, above). Melting Point: 135.3°–136.9° C.

Preparation 12

This description illustrates the preparation of 1-(2-bromo-6-cyano-4-difluoromethoxyphenyl)-4-pentafluoroethylpyrimidin-6-one. 1-(2-Amino-6-cyano-4-difluoromethoxyphenyl)-4-pentafluoroethylpyrimidin-6-one (the product of Preparation 11 Step 1) was converted to 1-(2-bromo-6-cyano-4-difluoromethoxyphenyl)-4-pentafluoroethylpyrimidin-6-one using the general method illustrated in Preparation 5 of EP 0 398 499 (see Preparation 1, Step 3, above). In this Example copper (II) bromide was used as the halide source. Melting Point: 124.0°–125.4° C.

Preparation 13

This description illustrates the preparation of 1-(2-bromo-6-cyano-4-trifluoromethoxyphenyl)-4-trifluoromethylpyrimidin-6-one.

1-(2-Amino-6-cyano-4-trifluoromethoxyphenyl)-4-trifluoromethyl-pyrimidin-6-one (Preparation 9 step 1) was converted to 1-(2-bromo-6-cyano-4-trifluoromethoxyphenyl)-4-trifluoromethylpyrimindin-6-one using the general method illustrated in Preparation 5 of EP 0 398 499 (see Preparation 1, Step 3, above). In this Example copper (II) bromide was used as the halide source. Melting point: 136.5°–137.2° C.

Preparation 14

This description illustrates the preparation of 1-(2-chloro-6-cyano-4-trifluoromethoxyphenyl)-4-pentafluoroethylpyrimidin-6-one.

Step 1

1-(2-Cyano-6-nitro-4-trifluoromethoxyphenyl)-4-pentafluoroethylpyrimidin-6-one (Preparation 5d) was converted to 1-(2-amino-6-cyano-4-trifluoromethoxyphenyl)-4-pentafluoroethylpyrimidin-6-one using the general procedure illustrated in Preparation 12 of EP 0 398 499 (see Preparation 2, Step 1, above). $^1$H NMR δ(CDCl$_3$ d$^6$DMSO): 8.10(1H,s); 7.03(1H,s); 7.02(1H,s); 6.93(1H,s); 5.23(1H,broad d).

Step 2

1-(2-Amino-6-cyano-4-trifluoromethoxyphenyl)-4-pentafluoroethyl-pyrimidin-6-one (step 1) was converted to 1-(2-chloro-6-cyano-4-trifluoromethoxyphenyl)-4-pentafluoroethylpyrimidin-6-one using the general method illustrated in Example 5 of EP 0 398 499 (In such Example, Lawesson's Reagent (2,4-bis-(4-methoxyphenyl-1,3-dithia-2,4-diphosphetane-2,4-disulphide) (0.58 g) was added to a stirred solution of 1-(2-chloro-6-cyano-4-trifluoromethylphenyl)-4-trifluoromethylpyrimidin-6-one (0.3 g) in dry, distilled pyridine (1 ml). The reaction mixture was heated to 130° C. for 16 hours, followed by further heating to 140° C. for 8 hours. After cooling to ambient temperature, the reaction mixture was dissolved in ethyl acetate, and washed with brine. After drying over anhydrous magnesium sulphate, evaporation of the solvent, under reduced pressure, gave a brown oil. This material was subjected to medium pressure liquid chromatography, on a Gilson apparatus, using silica gel as the stationary phase, eluting first with hexane containing ethyl acetate (5% by volume) and then with hexane containing ethyl acetate (2% by volume). The appropriate fractions were collected to give 1-(2-chloro-6-cyano-4-trifluoromethylphenyl)-4-trifluoromethylpyrimidin-8-thione as an organe solid.) $^1$H NMR $\delta$(CDCl$_3$): 8.08(1H,s); 7.77(1H,d); 7.67(1H,d); 7.08(1H,s).

EXAMPLE 1

This Example illustrates the preparation of 1-(2-chloro-6-amido-4-trifluoromethylphenyl)-4-pentafluoroethylpyrimidin-6-one (Compound No 1 of Table 1).

1-(2-Chloro-6-cyano-4-trifluoromethylphenyl)-4-pentafluoroethylpyrimidin-6-one (0.50 g; Example 2 c of EP 0 398 499) in concentrated sulphuric acid (2.5 cm$^3$) containing water (0.5 cm$^3$) was heated to 50° C. with stirring for 3 hours. The mixture was cooled, poured into water (100 cm$^3$), extracted with ethyl acetate (3×100 cm$^3$). The combined extracts were dried (magnesium sulphate) and evaporated under reduced pressure and the residue fractionated by eluting through a short column of silica with hexane/ethyl acetate (7:3 by volume) to give the desired product as colourless solid. Melting point: 195.5°–196.0° C.; $^1$H NMR $\delta$(CDCl$_3$): 5.67, 6.15 (2H, broad singlets); 7.00(1H,s); 7.98(1H,d); 8.00(1H,d); 8.10(1H,s).

EXAMPLE 2

This Example illustrates the preparation of 1-(2chloro-6-thioamido-4-trifluoromethylphenyl)-4-pentafluoroethylpyrimidin-6-one (Compound No 2 of Table 1).

1-(2-Chloro-6-cyano-4-trifluoromethylphenyl)-4-pentafluoroethylpyrimidin-6-one (0.2 g) and thioacetamide (0.072 g) in dry N,N-dimethylformamide (8 cm$^3$) was stirred and heated to 98° C. Dry hydrogen chloride gas was bubbled into the stirred solution for 2 hours, p-toluene sulphonic acid (0.091 g) was added and the mixture was heated for a further 2 hours. The organic solution was allowed to cool to ambient temperature, stored for 18 hours, poured into water (100 cm$^3$) and aqueous sodium hydrogen carbonate solution was added until the solution was at pH 6–7. The mixture was extracted with ethyl acetate (3×100 cm$^3$) and the combined extracts were washed with water (2×100 cm$^3$), dried (magnesium sulphate) and evaporated under reduced pressure to give a yellow-orange residue. The residue was fractionated using thick layer chroamtography (silica; hexane/ethyl acetate, 7:3 by volume) to give the desired product as a yellow solid. Melting Point: 158°–163° C. (with decomposition); $^1$H NMR $\delta$(CDCl$_3$) 7.00(1H,s); 7.46–7.56(2H,broad singlets); 7.79(1H,d); 7.90(1H,d), 8.09(1H,s).

EXAMPLE 3

This Example illustrates the preparation of 1-(2-carboxamido-6-chloro-4-trifluoromethylphenyl)-4-trifluoromethylpyrimidin-6-one (Compound No 3 of Table 1).

1-(2-Chloro-6-cyano-4-trifluoromethylphenyl)-4-trifluoromethylpyrimidin-6-one (0.997 g; Example 2 a of EP 0 398 499) was dissolved with stirring in concentrated sulphuric acid (5 cm$^3$) containing water (1 cm$^3$). The mixture was heated to 45° C. for 3 hours, cooled and stored for 18 hours at ambient temperature and re-heated to 50° C. for a further 2 hours. The mixture was cooled to ambient temperature, poured into water (50 cm$^3$) and extracted with ethyl acetate (3×100 cm$^3$). The combined organic fractions were washed with water (2×100 cm$^3$), dried (magnesium sulphate) and the residue recrystallised from hexane/ethyl acetate to give the desired product as a colourless solid. Melting Point: 236.0°–236.2° C.; $^1$H NMR $\delta$(d$_6$DMSO) 7.15(1H,s); 7.75–8.30(2H,broad singlets); 8.19(1H,d); 8.40(1H,d); 8.69(1H,s).

EXAMPLE 4

This Example illustrates the preparation of 1-(2-chloro-6-thioamido-4-trifluoromethylphenyl)-4-trifluoromethylpyrimidin-6-one (Compound No 4 of Table 1).

1-(2-Chloro-6-cyano-4-trifluoromethylphenyl)-4-trifluoromethylpyrimidin-6-one (0.50 g) in dry N,N-dimethylformamide (15 cm$^3$) was stirred and treated with thioacetamide (0.196 g) and p-toluene sulphonic acid (0.259 g). The mixture was heated to 90° C. for 5 hours, and then dry hydrogen chloride gas bubbled into the reaction at 90° C. for 3 hours. The reaction mixture was cooled to ambient temperature, treated with water (80 cm$^3$) and aqueous sodium hydrogen carbonate added until the solution was at pH 6–7.

The mixture was extracted with diethyl ether (3×150 cm), the combined extracts washed with water (2×150 cm$^3$), dried (magnesium sulphate) and evaporated under reduced pressure to give an orange solid. The solid was fractionated using column chromatography (silica; hexane/ethyl acetate, 7:3 by volume) to give the desired product as a pale yellow solid. Melting Point: 169.4°–169.8° C.; $^1$H NMR $\delta$(CDCl$_3$) 6.96(1H, broad s); 7.46–7.57 (2H, broad singlets); 7.79(1H,d); 7.90(1H,d); 8.10(1H,6s)

EXAMPLE 5

The following compounds were made according to the general procedure illustrated in Example 4.

a) 1-(2-Bromo-6-thioamido-4-trifluoromethylphenyl)-4-trifluoromethylpyrimidin-6-one (Compound No. 5 in Table I) from 1-(2-bromo-6-cyano-4-trifluoromethylphenyl)-4-trifluoromethylpyrimidin-6-one (the product of Example 2d of EP 0 398 499; this Example involved the preparation of such compound by the reaction of 3-bromo-5-fluoro-5-cyano-trifluoromethylbenzene and 4-trifluoromethylpyrimidin-6-one in accordance with the general method described in Preparation 3, above. Melting point: 193°–195° C.; $^1$H NMR δ(CDCl$_3$): 8.10(1H,s); 8.06(1H,s); 7.81(1H,s); 7.60(1H,broad s); 7.52(1H,broad s); 6.96(1H,s).

b) 1-(2-Bromo-6-thioamido-4-trifluoromethylphenyl)-4-pentafluoroethylpyrimidin-6-one (Compound No. 6 in Table I), from 1-(2-bromo-6-cyano-4-trifluoromethylphenyl)-4-pentafluoromethylpyrimidin-6-one (Example 2e of EP 0 398 499; this Example involved the preparation of such compound by the reaction of 3-bromo-4-fluoro-5-cyanotrifluoromethylbenzene and 4-pentafluoroethylpyrimidin-6-one in accordance with the general method described in Preparation 3, above.) Melting point: 162°–164° C.: $^1$H NMR δ(CDCl$_3$): 8.10(1H,s); 8.07(1H,s); 7.84(1H,s); 7.59(1H,broad s); 7.48(1H,broad s); 7.03(1H,s).

c) 1-(2-Chloro-6-thioamido-4-trifluoromethylphenyl)-5-methyl-4-trifluoromethylpyrimidin-6-one (Compound No. 7 in Table I) from 1-(2-chloro-4-trifluoromethylphenyl-5-methylpyrimidin-6-one (Preparation 3a). Melting point: 192.6°–4.8° C.: $^1$H NMR δ(CDCl$_3$): 7.95(1H,s); 7.90(1H,d); 7.80(1H,d); 7.50(2H,broad s); 2.30 (3H,m).

d) 1-(2-Bromo-6-thioamido-4-trifluoromethylphenyl)-5-methyl-4-pentafluoromethylpyrimidin-6-one (Compound No. 8 in Table I) from 1-(2-bromo-6-cyano-4-trifluoromethylphenyl)-5-methyl-4-pentafluoroethylpyrimidin-6-one (Preparation 3b). Melting point: 200.6°–201.1° C.: $^1$H NMR δ(CDCl$_3$); 8.05(1H,d); 7.85(1H,d); 7.50(2H,broad s); 7.92(1H,s); 2.30(3H,m).

e) 1-(2-Chloro-6-thioamido-4-trifluoromethylphenyl)-5-methyl-4-pentafluoroethylpyrimidin-6-one (Compound No. 9 in Table I) from 1-(2-chloro-6-cyano-4-trifluoromethylphenyl)-5-methyl-4-pentafluoroethylpyrimidin-6-one. Melting point: 206°–208° C.: $^1$H NMR δ(CDCl$_3$): 7.95(1H,s); 7.90(1H,d); 7.8(1H,d); 7.55(2H,broad s); 2.30 (3H,m).

f) 1-(2-Fluoro-6-thioamido-4-trifluoromethylphenyl)-4-trifluoromethylpyrimidin-6-one (Compound No. 10 in Table 1) from 1-(2-cyano-6-fluoro-4-trifluoromethylphenyl-4-trifluoromethylpyrimidin-6-one (Example 6 of EP 0 398 499 or Preparation 6). $^1$H NMR δ(CDCl$_3$): 8.16(1H,s); 7.70(1H,s); 7.64(1H,d); 7.60(1H,broad s); 7.45(1H,broad s); 6.94(1H,s).

g) 1-(2-Fluoro-6-thioamido-4-trifluoromethylphenyl)-5-methyl-4-pentafluoroethylpyrimidin-6-one (Compound No. 11 in Table I) from 1-(2-cyano-6-fluoro-4-trifluoromethylphenyl)-5-methyl-4-pentafluoroethylpyrimidin-6-one (Preparation 7a) $^1$H NMR δ(CDCl$_3$): 8.01(1H,s); 7.73(2H,broad s); 7.68(1H,s); 7.61(1H,d); 2.31(3H,t).

h) 1-(2-Fluoro-6-thioamido-4-trifluoromethylphenyl)-5-methyl-4-trifluoromethylpyrimidin-6-one (Compound No. 12 in Table I) from 1-(2-cyano-6-fluoro-4-trifluoromethylphenyl)-5-methyl-4-trifluoromethylpyrimidin-6-one (Preparation 7b). $^1$H NMR δ(CDCl$_3$): 8.01(1H,s); 7.70(1H,s); 7.62(1H,d); 7.60 (1H,broad s); 7.52(1H,broad s): 2.31(3H,d).

i) 1-(4-Difluoromethoxy-2-fluoro-6-thioamidophenyl)-4-pentafluoroethylpyrimidin-6-one (Compound No. 13 in Table I) from 1-(2-cyano-4-difluoromethoxy-6-fluorophenyl)-4-pentafluoroethylpyrimidin-6-one (Preparation 8).

$^1$H NMR δ(CDCl$_3$): 8.15(1H,s); 7.57 (1H,broad s); 7.48(1H, broad s); 7.20–7.14 (2H complex); 6.97(1H,s); 6.62(1H,t).

j) 1-(2-Chloro-6-thioamido-4-trifluoromethoxyphenyl)-4-trifluoromethylpyrimidin-6-one (Compound No. 14 in Table I) from 1-(2-chloro-6-cyano-4-trifluorome- thoxyphenyl)-4-trifluoromethylpyrimidin-6-one (Preparation 9). $^1$H NMR δ(CDCl$_3$): 8.11(1H,s); 7.62(2H,broad s); 7.50(1H,d); 7.38(1H,d); 6.95(1H,s).

k) 1-(2-Chloro-4-[1′,1′,2′,2′-tetrafluoroethoxy]-6-thioamidophenyl)-4-trifluoromethylpyrimidin-6-one (Compound No. 15 in Table I) from 1-(2-chloro-6-cyano-4-[1′,1′,2′,2′-tetrafluoroethoxy]phenyl)-4-trifluoromethylpyrimidin-6-one (Preparation 10). $^1$H NMR δ(CDCl$_3$): 8.10(1H,s); 7.59(1H broad s); 7.52(1H, broad s); 7.52(1H,d); 7.40(1H, d); 6.95(1H, s); 5.98 (1H,tt).

l) 1-(2-Chloro-4-difluoromethoxy-6-thioamidophenyl)-4-pentafluoroethylpyrimidin-6-one (Compound No. 16 in Table I) from 1-(2-chloro-6-cyano-4-difluoromethoxyphenyl)-4-pentafluoroethylpyrimidin-6-one (Preparation 11). $^1$H NMR δ(CDCl$_3$): 8.10(1H,s); 7.52(2H, broad s); 7.43(1H,d); 7.32(1H,d); 7.00(1H,s); 6.62(1H,t).

m) 1-(2-Bromo-4-difluoromethoxy-6-thioamidophenyl)-4-pentafluoromethylpyrimidin-6-one (Compound No. 17 in Table I) from 1-(2-bromo-6-cyano-4-difluoromethoxyphenyl)-4-pentafluoroethylpyrimidin-6-one (Preparation 12). $^1$H NMR δ(CDCl$_3$): 8.08(1H,s); 7.59(1H,d); 7.54(2H, broad s): 7.35 (1H,d); 7.00(1H,s); 6.63(1H,t).

n) 1-(2-Bromo-6-thioamido-4-trifluoromethoxyphenyl)-4-trifluoromethylpyrimidin-6-one (Compound No. 25 in Table I) from 1-(2-bromo-6-cyano-4-trifluoromethoxyphenyl)-4-trifluoromethylpyrimidin-6-one (Preparation 13). Melting Point: 170.5°–171.2° C.: $^1$H NMR δ(CDCl$_3$): 8.10(1H,s); 7.67(1H,d): 7.52(1H, broad s): 7.48 (1H, broad s): 7.46 (1H,d); 6.96(1H,s).

o) 1-(2-Fluoro-6-thioamido-4-trifluoromethoxyphenyl)-4-trifluoromethylprimidin-6-one (Compound No. 26 in Table I) from 1-(2-cyano-6-fluoro-4-trifluoromethoxyphenyl)-4-trifluoromethylpyrimidin-6-one (Preparation 7c). Melting point: 116°–117° C.: $^1$H NMR δ(CDCl$_3$): 8.17(1H,s); 7.56 (1H, broad s); 7.43 (1H, broad s); 7.29(1H, s); 7.23(1H,s); 6.94(1H,s).

p) 1-(2-Chloro-6-thioamido-4-trifluoromethoxyphenyl)-4-pentafluoroethylpyrimidin-6-one (Compound No. 27 in Table I) from 1-(2-chloro-6-cyano-4-trifluoromethoxyphenyl)-4-pentafluoroethylpyrimidin-6-one (Preparation 14). Melting Point: 150° C. (decomp): $^1$H NMR δ(CDCl$_3$): 8.10(1H,s); 7.54(1H, broad s); 7.51(1H,s); 7.46(1H, broad s); 7.40(1H,d); 7.00(1H,s).

q) 1-(2-Fluoro-6-thioamido-4-trifluoromethoxyphenyl)-4-pentafluoroethylpyrimidin-6-one (Compound No. 28 in Table I) from 1-(2-cyano-6-fluoro-4-trifluoromethoxyphenyl)-4-pentafluoroethylpyrimidin-6-one (Preparation 7d). Melting Point: 170° C. (decomp): $^1$H NMR δ(CDCl$_3$): 8.17(1H,s); 7.60(1H, broad s); 7.53(1H, broad s); 7.28(1H,s); 7.24(1H,s); 6.99(1H,s).

r) 1-(2-Chloro-6-thioamido-4-trifluoromethylphenyl)-5-bromo-4-trifluoromethyl-2-pyridone (Compound No. 32 in Table II) from 1-(2-Chloro-6-cyano-4-trifluoromethylphenyl)-5-bromo-4-trifluoromethyl-2-pyridone (Compound No. 16 in EP 0 398 499). $^1$H NMR δ(CDCl$_3$): 7.85(2H, broad s); 7.81(1H,s); 7.60(1H, broad s); 7.50(1H,s); 7.08(1H,s).

EXAMPLE 6

This Example illustrates the preparation of 1-(2-[N-methyl]-carboxamido-6-chloro-4-trifluoromethylphenyl)-4-trifluoromethylpyrimidin-6-one (Compound No. 29 of Table 1).

Stage 1: Preparation of
3-chloro-2-(6-oxo-4-trifluoromethyl-6H-pyrimidin-1-
yl)-5-trifluoromethylbenzoic acid 1-(2-Carboxamido-6-chloro-4-trifluoromethyl-
phenyl)-4-trifluoromethylpyrimidin-6-one (3.0 g, Example 3) was dissolved in trifluoroacetic acid (50 cm$^3$). A solution of sodium nitrile (2.67 g) in water (5 cm$^3$) was then added dropwise-the slight exotherm being controlled by judious use of an ice bath. After the addition was complete, the stirred reaction mixture was allowed to warm to the ambient temperature, and allowed to stand for 48 hours. The reaction mixture was then poured into water (200 cm$^3$), resulting in the formation of a white precipitate. The pH of the mixture was adjusted to mild acidity by the addition of aqueous sodium carbonate solution, whereupon the precipitate was collected at the pump, and air dried to give the desired product as white solid. Melting Point: 224.8°–225.3° C.; $^1$H NMR $\delta$(d$^6$DMSO) 8.75(s,1H); 8.55(d,1H); 8.30(d,1H); 7.25(s,1H).

Stage 2/3: Preparation of
1-(2-[N-methyl]-carboxamido-6-chloro-4-trifluorome-
thylphenyl)-4-trifluoromethylpyrimidin-6-one 3-chloro-2-(6-oxo-4-trifluoromethyl-6H-pyrimidin-1-yl)-5-trifluoromethylbenzoic acid (Stage 1, 2.1 g), in thionylchloride (20 cm$^3$) was heated to reflux for a period of 5 hours, in the presence of dimethylformamide (2 drops). Excess thionyl chloride was then removed by evaporation under reduced pressure, to afford a white solid. This was the added to a cooled (−76° C.) saturated solution of methylamine in diethyl ether. After allowing to warm to −50° C., and then to the ambient temperature, the solvent, and excess amine, were removed by evaporation under reduced pressure to give a white solid. This was recrystallised from hexane containing a small amount of ethyl acetate, to give a white solid, identified as the phenyl-substituted amino crotonamide. $^1$H NMR $\delta$(d$^6$DMSO) 9.75(broad s, 1H); 8.40(broad s, 1H; 8.00(d,1H); 7.70(d,1H); 7.50(broad s,2H); 5.35(s,1H); 2.65(d,3H).

Phosphorous oxychloride (0.068 cm$^3$) was added to ice-cooled dry dimethylformamide (0.061 cm$^3$), and the mixture diluted with dry 1,2-dichloroethane (5 cm$^3$). The stirred mixture was heated to 80° C. for 30 minutes, and cooled to the ambient temperature, whereupon the above phenyl-substituted amino crotonamide product dissolved in 1,2-dichloroethane (5 cm$^3$) was added. The reaction mixture was then heated to 85° C. for 2 hours, cooled, and poured into water (50 cm$^3$). The mixture was extracted into ethyl acetate, and the combined organic extracts water washed, dried, and concentrated by evaporation of the solvent under reduced pressure, to afford a yellow solid. This was subjected to preparative thin layer chromatography on silica gel, using hexane containing 30% by volume ethyl acetate to give the desired product as a white solid. $^1$H NMR $\delta$(CDCl$_3$) 8.12(s,1H); 7.95(d,1H); 7.8(d,1H); 6.95(s,1H); 6.2(broad s,1H); 2.90(s,3H).

EXAMPLE 7

This Example illustrates the preparation of 1-(2-[N,N-dimethyl]-carboxamido-6-chloro-4-trifluoromethyl-phenyl)-4-trifluoromethylpyrimidin-6-one (Compound No. 20 in Table I).

of 3-chloro-2-(6-oxo-4-trifluoromethyl-6H-pyrimidin-1-yl)-5-trifluoromethylbenzoic acid. (Example 6, Stage 1, 0.1 g), in thionyl chloride (1 cm$^3$), was heated to reflux for a period of 5 hours, in the presence of dimethylformamide (2 drops). Excess thionyl chloride was then removed by evaporation under reduced pressure affording a yellow solid. This intermediate acid chloride was dissolved in dry diethyl ether, and to the solution was added excess dimethylamine. After a short period, the solvent and excess dimethylamine was removed by evaporation under reduced pressure to give an off-white solid. This was partitioned between ethyl acetate and water. The aqueous washings were reextracted with ethyl acetate, and the combined organic extracts were dried, filtered, and concentrated by evaporation of the solvent, under reduced pressure, to give the desired product as a white solid. Melting Point: 199.5°–200° C.; $^1$H NMR $\delta$(CDCl$_3$) 8.12(s,1H); 7.91(d,1H); 7.60(d,1H); 6.90(s,1H); 3.00(s,3H); 2.95(s,3H).

EXAMPLE 8

This Example illustrates the preparation of 1-(2-chloro-6-[N,N-dimethyl]-thioamido-4-trifluoromethyl-phenyl)-4-trifluoromethylpyrimidin-6-one (Compound No. 21 in Table I).

A solution of 1-(2-[N,N-dimethyl]-carboxamido-6-chloro-4-trifluoromethylphenyl)-4-trifluoromethyl-pyrimidin-6-one (0.3 g, Example 7), and Lawesson's reagent [2,4-bis (4-methoxyphenyl)-1,3-dithia-2,4-diphosphetane-2,4-disulphide] (0.348 g) in dry toluene (6 cm$^3$) was heated to 110° C. for a total of 20 hours. After cooling to the ambient temperature, the reaction mixture was poured into water, and extracted with ethyl acetate. The organic extract was water washed, dried, and concentrated by evaporation of the solvent, under reduced pressure, to afford a yellow solid. The crude product was then purified by extensive column chromatography on silica gel, using hexane containing ethyl acetate (20% by volume), to give the desired product containing a small amount of the starting amide. $^1$H NMR $\delta$(CDCl$_3$) 8.20(s,1H); 7.85(d,1H); 7.45(d,1H); 6.90(s,1H); 3.45(s,3H); 3.2(s,3H).

EXAMPLE 9

This Example illustrates the preparation of 1-(2-[N,N-dimethyl]-carboxamido-6-chloro-4-trifluoromethyl-phenyl)-4-pentafluoromethylpyrimidin-6-one (Compound No. 22 in Table I).

Stage 1: Preparation of
3-chloro-2-(6-oxo-4-pentafluoroethyl-6H-pyrimidin-1-
yl)-5-trifluoromethyl-benzoic acid 1-(2-Carboxamido-6-chloro-4-trifluoromethyl-phenyl)-4-pentafluoromethylpyrimidin-6-one (Example 1, 2.63 g) was reacted according to the procedure given in Stage 1 of Example 6 to give the desired product, again as a white solid. Melting Point: 189°–190° C.; $^1$H NMR $\delta$(d$^6$DMSO) 8.80(s,1H); 8.60(d,1H); 8.35(d,1H); 7.20(s,1H).

Stage 2

The product of stage 1 (1 g) was reacted according to the method given in Example 7, to give the desired product as a pale yellow solid. Melting Point: 146.6°–147.4° C.; $^1$H NMR $\delta$(CDCl$_3$) 8.12(s,1H); 7.95(d,1H); 7.60(d,1H); 6.95(s,1H); 3.05(s,3H); 2.95(s,3H).

EXAMPLE 10

This Example illustrates the preparation of 1-2[N,N-dimethyl]-thioamido-6-chloro-4-trifluoromethylphenyl)-4-pentafluoromethylpyrimidin-6-one (Compound No. 23 in Table 1).

1-(2-[N,N-dimethyl]-carboxamido-6-chloro-4-trifluoromethylphenyl)-4-pentafluoroethylpyrimidin-6-one (Example 9) was reacted according to the method given in Example 8, to give the desired product as a pale yellow solid. Melting Point: 198°–199° C.; $^1$H NMR δ(CDCl$_3$) 8.19(s,1H); 7.85(d,1H); 7.45(d,1H); 6.92(s,1H); 3.45(s,3H); 3.21(s,3H).

EXAMPLE 11

This Example illustrates the preparation of 1-(2-[N-methyl]-thioamido-6-chloro-4-trifluoromethylphenyl)-4-trifluoromethylpyrimidin-6-one (Compound No. 18 in Table I).

1-(2-[N-methyl]-carboxamido-6-chloro-4-trifluoromethylphenyl)-4-trifluoromethylpyrimidin-6-one (Example 6) was converted, accorded to the procedure given in Example 8, into the desired product. Melting Point: 211.9°–213.2° C.; $^1$H NMR δ(CDCl$_3$) 8.10(s,1H); 7.90(broad s,1H); 7.88(d,1H); 7.70(d,1H); 6.93(s,1H); 3.18(d,3H).

The following compound was also isolated as a by-product from this reaction.

1-(2-N-methyl]-thioamido-6-chloro-4-trifluoromethyl)phenyl-4-trifluoromethyl)pyrimidin-6-thione (Compound No. 19 in Table I). Melting Point: 168°–169° C.; $^1$H NMR δ(CDCl$_3$) 8.20(s,1H); 8.10(broad s,1H); 7.89(s,1H); 7.71(s,1H); 3.15(d,1H).

EXAMPLE 12

This Example illustrates the preparation of 1-(2-chloro-6-thioamido-4-trifluoromethylphenyl)-4-trifluoromethylpyrimidin-6-thione (Compound No. 24 in Table I).

1-(2-Amido-6-chloro-4-trifluoromethylphenyl)-4-trifluoromethylpyrimidin-6-one (0.080 g, Example 3), and Lawesson's reagent (0.930 g) in dry toluene (80 cm$^3$) was heated to 90° C. for a period of 2 hours. After cooling to the ambient temperature, the reaction mixture was filtered, and the filtrate concentrated by evaporation of the solvent, under reduced pressure, to afford a yellow solid. Preparative thin layer chromatography on silica, using petroleum ether (boiling range 60°–80° C.) containing ethyl acetate (20% by volume), to give the desired product as a pale yellow solid. Melting Point: 149°–151° C.; $^1$H NMR δ(CDCl$_3$) 8.21(s,1H); 7.89(s,1H); 7.82(s,1H); 7.75(s,1H); 7.71(broad s,1H); 7.58(broad s,1H).

EXAMPLE 13

The activity of the compounds of formula (I) was determined using a variety of pests. The pests were treated with a liquid composition containing 500 parts per million (ppm) by weight of the compound unless otherwise stated. The compositions were made by dissolving the compound in acetone and diluting the solutions with water containing 0.01% by weight of a wetting agent sold under the trade name "SYNPERONIC" NX until the liquid composition contained the required concentration of the compound. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the medium and the pests with the compositions. The mortality of the pests was then assessed at periods usually varying from one to three days after the treatment.

The results of the tests are presented in Table V for each of the compounds at the rate in parts per million given in the second column. The results indicate a grading of mortality designated as A, B or C wherein A indicates 80–100% mortality, B indicates 50–79% mortality and C indicates less than 50% mortality.

Information regarding the pest species, the support medium or food, and the type and duration of the test is given in Table VI. The pest species is designated by a letter code.

In Table VI the pest organism used is designated by a letter code and the pest species, the support medium or food, and the type and duration of test is given.

TABLE V

| COMPOUND | RATE OF APPLICATION ppm | SPECIES MD (see Table VI) | SPECIES BG (see Table VI) |
| --- | --- | --- | --- |
| 1 | 500 | A | B |
| 2 | 500 | A | B |
| 3 | 500 | A | A |
| 5 | 500 | A | A |
| 6 | 500 | A | A |
| 7 | 500 | A | A |
| 8 | 500 | A | A |
| 9 | 500 | A | A |
| 10 | 500 | A | A |
| 11 | 500 | A | A |
| 12 | 500 | A | A |
| 13 | 500 | A | A |
| 14 | 500 | A | A |
| 15 | 500 | A | A |
| 16 | 500 | A | A |
| 17 | 500 | A | A |
| 18 | 500 | A | A |
| 19 | 500 | A | A |
| 21 | 500 | A | C |
| 22 | 500 | A | A |
| 23 | 500 | A | A |
| 24 | 500 | A | A |

TABLE VI

| CODE LETTERS | TEST SPECIES | SUPPORT MEDIUM/FOOD | TYPE OF TEST | DURATION (days) |
| --- | --- | --- | --- | --- |
| MD | Musca domestica (houseflies - adults) | Cotton wool/ sugar | Contact | 2 |
| BG | Blattella germanica (cockroach nymphs) | Plastic pot/ calf weaner pellets | Contact | 3 |

FORMULAE
(in description)

(I) $\underset{R^1}{\underset{R^2}{\overset{R^3}{\bigcirc}}}\overset{R^4}{\underset{X}{\overset{R^5}{-}}}\overset{O}{\underset{X}{C}}-NY^1Y^2$ (a) Pyridine ring with $R^{20}, R^{21}, R^{22}, R^{23}, R^{10}$ substituents, N-linked (b) $R^{24}, R^{25}, R^{26}, R^{10}$ substituted ring, N-linked (c) Pyrazole with $R^{27}, R^{28}, R^{29}$ (d) Ring with $R^{30}, R^{31}, R^{32}$ (e) Triazole with $R^{33}, R^{34}$ (b') Ring with $R^{25}, R^{26}, R^{10}$ (a') Pyridinone with $R^{21}, R^{22}, R^{23}$ (e') Triazole with $R^{33}, R^{34}$ (c') Pyrazole with $R^{27}, R^{28}$ -continued
FORMULAE
(in description)

(II) $\underset{R^{36}}{\underset{R^1}{\underset{R^2}{\overset{R^3}{\bigcirc}}}}\overset{R^4}{\underset{X}{\overset{R^5}{-}}}\overset{O}{\underset{X}{C}}-NY^1Y^2$ (III) $H-R^1$ (A) $\underset{R^1}{\underset{R^2}{\overset{R^3}{\bigcirc}}}\overset{R^4}{\overset{R^5}{-}}CN$

Scheme 1

$\underset{R^1}{\underset{R^2}{\overset{R^3}{\bigcirc}}}\overset{R^4}{\overset{R^5}{-}}\overset{O}{\underset{X}{C}}-NH_2$ ↓ (a) Aqueous sodium nitrite in the presence of Trifluoracetic acid acting both as solvent and acid.

$\underset{R^1}{\underset{R^2}{\overset{R^3}{\bigcirc}}}\overset{R^4}{\overset{R^5}{-}}\overset{O}{\underset{X}{C}}-OH$ ↓ (b) $Y^1Y^2NH$ in the presence of a dehydrating agent $\underset{R^1}{\underset{R^2}{\overset{R^3}{\bigcirc}}}\overset{R^4}{\overset{R^5}{-}}\overset{O}{\underset{X}{C}}-NY^1Y^2$

Scheme 2

$\underset{R^1}{\underset{R^2}{\overset{R^3}{\bigcirc}}}\overset{R^4}{\overset{R^5}{-}}\overset{O}{\underset{X}{C}}-NY_1Y^2$ ↓ (a) Treatment with a chlorinating agent

Scheme 2

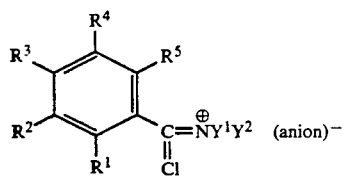 (anion)⁻

↓ (b) H₂S

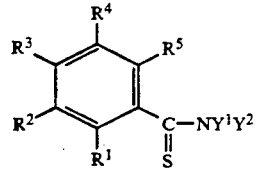

Scheme 2'

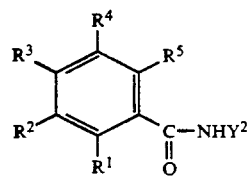

↓ (a) Treatment with a chlorinating agent

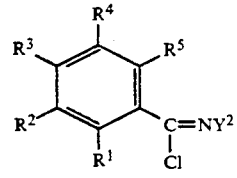

↓ (b) H₂S

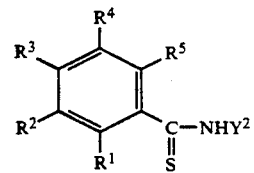

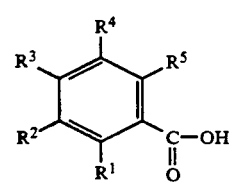

We claim:

1. An insecticidal compound of formula (I):

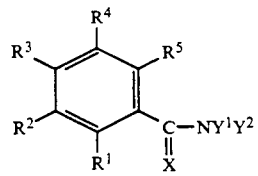

wherein $R^1$ is of the formula:

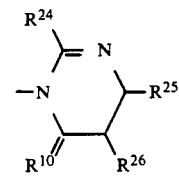

where $R^{10}$ is oxygen or sulphur; $R^{24}$ is hydrogen, halogen, $NR^7N^8$, $S(O)_nR^6$, $C_{1-6}$ alkyl or $C_{3-10}$ cycloalkyl wherein $R^7$ and $R^8$ are independently selected from hydrogen, $C_{1-6}$ alkyl or $C_{3-10}$ cycloalkyl; $R^{25}$ is halo, nitro, $C_{1-6}$ haloalkyl, $C_{1-6}$ haloalkoxy or $S(O)_nR^6$; and $R^{26}$ is hydrogen, $C_{1-6}$ alkyl, halogen, cyano, $C_{1-6}$ hydroxyalkyl, $C_{1-6}$ alkoxy, $S(O)_nR^6$, $C_{1-6}$ haloalkylthio, $NR^{11}R^{12}$, formyl, nitro or $C_{1-6}$ haloalkyl; $R^2$ is hydrogen, halogen, $C_{1-6}$ haloalkyl, nitro, or cyano; $R^3$ and $R^5$ are independently selected from hydrogen, halogen, $C_{1-6}$ alkyl or $C_{3-10}$ cycloalkyl; $R^4$ is halogen, $C_{1-6}$ haloalkyl, $C_{1-6}$ haloalkoxy or $S(O)_nR^6$ where $R^6$ is $C_{1-6}$ alkyl, $C_{1-6}$ haloalkyl or $C_{3-10}$ cycloalkyl and n is 0, 1 or 2; X is O or S and $Y^1$ and $Y^2$ are independently selected from hydrogen, nitro, amino or $C_{1-6}$ alkyl optionally substituted by halogen, by $C_{3-10}$ cycloalkyl, by formyl, by $C_{2-7}$ alkanoyl, by $C_{4-7}$ cycloalkylcarbonyl, by $C_{2-7}$ alkoxycarbonyl, by $C_{2-7}$ haloalkoxycarbonyl, or by an phenyl group or $Y^1$ and $Y^2$ together form the group $=CHY^3$ wherein $Y^3$ is $C_{1-6}$ alkyl, $C_{2-6}$ alkenyl, phenyl, or amino optionally substituted by $C_{1-6}$ alkyl or $Y^1$ is hydrogen and $Y^2$ is $C_{1-6}$ alkoxycarbonyl, $C_{1-6}$ alkylcarbonyl, or a group $-S(O)_nR^6$ where $R^6$ and n are as hereinbefore defined.

2. A compound according to claim 1 wherein $R^2$ is fluorine, chlorine, bromine or trifluoromethyl.

3. A compound according to claim 1 wherein $R^3$ and $R^5$ are hydrogen.

4. A compound according to claim 1 wherein $R^4$ is trifluoromethyl, pentafluoroethyl, trifluoromethylthio, iodine, bromine, chlorine, fluoro $C_{1-4}$ alkoxy or $S(O)_nR^6$.

5. A compound according to claim 1 wherein $R^{25}$ is trifluoromethyl or pentafluoroethyl.

6. A compound according to claim 1 wherein $R^{24}$ is hydrogen.

7. A compound according to claim 1 wherein $R^{26}$ is hydrogen or alkyl.

8. A method of killing or controlling insect or acarine pests which method comprises applying to the pest or to the locus thereof an effective amount of a compound of formula (I) as defined in claim 1 or claims 2-7.

9. An insecticidal or acricidal composition comprising an effective amount of a compound of formula (I) as defined in claim 1 in combination with a diluent or carrier.

* * * * *